(12) United States Patent
Kawata

(10) Patent No.: US 11,229,412 B2
(45) Date of Patent: Jan. 25, 2022

(54) X-RAY IMAGING APPARATUS AND MONOCHROMATIC X-RAY GENERATING METHOD

(71) Applicant: CANON MEDICAL SYSTEMS CORPORATION, Otawara (JP)

(72) Inventor: Go Kawata, Nagareyama (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/073,584

(22) Filed: Oct. 19, 2020

(65) Prior Publication Data

US 2021/0121142 A1 Apr. 29, 2021

(30) Foreign Application Priority Data

Oct. 28, 2019 (JP) .............................. JP2019-195202

(51) Int. Cl.
| | |
|---|---|
| *A61B 6/00* | (2006.01) |
| *G01T 1/20* | (2006.01) |
| *A61B 6/04* | (2006.01) |
| *A61B 6/03* | (2006.01) |
| *H05G 1/02* | (2006.01) |

(52) U.S. Cl.
CPC .......... *A61B 6/4035* (2013.01); *A61B 6/0407* (2013.01); *A61B 6/4241* (2013.01); *A61B 6/482* (2013.01); *A61B 6/54* (2013.01); *G01T 1/2018* (2013.01); *H05G 1/02* (2013.01); *A61B 6/035* (2013.01); *A61B 6/0487* (2020.08)

(58) Field of Classification Search
CPC ... A61B 6/4035; A61B 6/4241; A61B 6/0407; A61B 6/54; A61B 6/482; A61B 6/0487; A61B 6/035; G01T 1/2018; G01T 7/005; G01T 1/2985; H05G 1/02; G21K 1/10
See application file for complete search history.

(56) References Cited

U.S. PATENT DOCUMENTS

| | | | |
|---|---|---|---|
| 7,330,535 B2* | 2/2008 | Arenson ................. | G21K 1/04 378/156 |
| 2005/0089146 A1* | 4/2005 | Toth ........................ | G21K 1/04 378/158 |
| 2014/0328453 A1* | 11/2014 | Hsieh .................. | G02B 26/023 378/16 |
| 2015/0160355 A1 | 6/2015 | Wang et al. | |

(Continued)

FOREIGN PATENT DOCUMENTS

| | | |
|---|---|---|
| JP | 2006-155925 A | 6/2006 |
| WO | WO-2016051996 A1 * | 4/2016 .............. A61B 6/06 |

*Primary Examiner* — Christine S. Kim
(74) *Attorney, Agent, or Firm* — Oblon, McClelland, Maier & Neustadt, L.L.P.

(57) ABSTRACT

An X-ray imaging apparatus according to an embodiment of the present disclosure includes an X-ray tube, a photon counting X-ray detector, and a filter unit. A generating unit of the X-ray tube is configured to generate X-rays. The photon counting X-ray detector is configured to count photons contained in the X-rays. The filter unit is provided between the X-ray tube and the photon counting X-ray detector. The filter unit includes a first filter and a second filter. The first filter is configured to shape a spectrum of the X-rays. The second filter is configured to generate X-ray fluorescence on the basis of X-rays related to a spectrum resulting from the shaping by the first filter.

11 Claims, 13 Drawing Sheets

(56) References Cited

U.S. PATENT DOCUMENTS

2016/0113617 A1    4/2016   Herrmann et al.
2016/0282487 A1    9/2016   Kawata et al.
2018/0333591 A1   11/2018   Silver
2019/0204462 A1    7/2019   Schu

* cited by examiner

X-RAY IMAGING APPARATUS AND MONOCHROMATIC X-RAY GENERATING METHOD

CROSS-REFERENCE TO RELATED APPLICATIONS

This application is based upon and claims the benefit of priority from Japanese Patent Application No. 2019-195202, filed on Oct. 28, 2019; the entire contents of which are incorporated herein by reference.

FIELD

Embodiments described herein relate generally to an X-ray imaging apparatus and a monochromatic X-ray generating method.

BACKGROUND

For bringing outputs of a photon counting detector into correspondence with energy levels, various methods are known including: a method by which the energy of the K-absorption edge is estimated by using an attenuation coefficient curve generated by measuring a transmission spectrum of a known substance; a method by which X-ray fluorescence occurring as a result of an interaction between the photon counting detector and X-rays is detected; and a method by which K-shell electrons in heavy metal are excited by X-rays so as to directly measure X-ray fluorescence corresponding to the K-absorption edge.

However, the position corresponding to the energy of the K-absorption edge in the attenuation coefficient curve varies depending on the energy resolution of the photon counting detector. For this reason, when the energy resolution of the handled photon counting detector fluctuates, it would be difficult to accurately implement energy calibration by simply measuring the energy of the K-absorption edge while using the attenuation coefficient curve. Further, to measure the X-ray fluorescence occurring inside the photon counting detector, it would be necessary to perform a simultaneous measuring process on two photon counting detectors. In that situation, increases in installation costs and/or data amounts are anticipated. Further, according to the method by which the K-shell electrons of metal are excited, it would be necessary to separate the X-ray fluorescence corresponding to the K-absorption edge from the exciting X-rays used on the K-shell electrons. Accordingly, depending on the thickness of the metal, the efficiency in extracting the X-ray fluorescence might be degraded.

DETAILED DESCRIPTION

Figure 1:
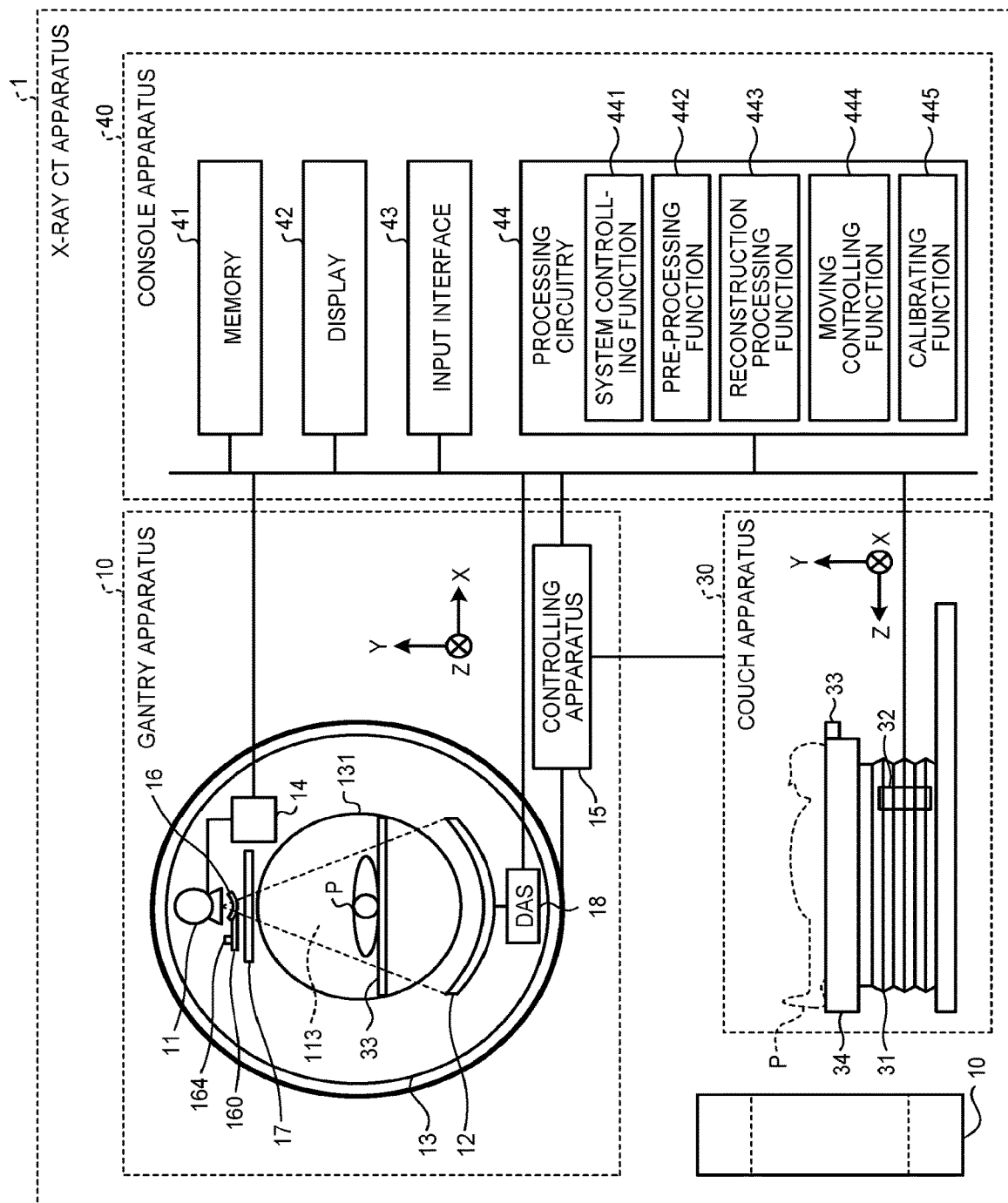
FIG. 1 is a diagram illustrating an exemplary configuration of an X-ray Computed Tomography (CT) apparatus according to an embodiment.

Exemplary embodiments of an X-ray imaging apparatus and a monochromatic X-ray generating method will be explained in detail below, with reference to the accompanying drawings. In the embodiments described below, some of the constituent elements having the same reference characters perform the same operations, and duplicate explanations thereof will be omitted as appropriate. Further, to explain the present disclosure more specifically, the X-ray imaging apparatus according to the embodiments will be explained as an X-ray Computed Tomography apparatus (hereinafter, "X-ray CT apparatus").

The X-ray CT apparatus described in the following embodiments is an apparatus capable of performing a photon counting CT process. In other words, an X-ray CT apparatus 1 described in the following embodiments is an apparatus capable of reconstructing X-ray CT image data having a high Signal-to-Noise (SN) ratio by counting X-rays that have passed through an examined subject (hereinafter "patient") by using, not a conventional integral-type detector (implementing an electric-current mode measuring method), but a detector implementing a photon counting method (hereinafter, "photon counting X-ray detector").

Embodiments

An X-ray imaging apparatus according to an embodiment includes an X-ray tube, a photon counting X-ray detector, and a filter unit. The X-ray tube is configured to generate X-rays. The photon counting X-ray detector is configured to count photons contained in the X-rays. The filter unit is provided between the X-ray tube and the photon counting X-ray detector. The filter unit includes a first filter and a second filter. The first filter is configured to shape a spectrum of the X-rays. The second filter is configured to generate X-ray fluorescence on the basis of X-rays related to a spectrum resulting from the shaping by the first filter.

FIG. 1 is a diagram illustrating an exemplary configuration of the X-ray CT apparatus 1 according to the present embodiment. As illustrated in FIG. 1, the X-ray CT apparatus 1 includes a gantry apparatus 10, a couch apparatus 30, and a console device 40. In the present embodiment, the rotation axis of a rotating frame 13 in a non-tilted state and the longitudinal direction of a couchtop 33 of the couch apparatus 30 are defined as a Z-axis direction; the axial direction orthogonal to the Z-axis direction and parallel to the floor surface is defined as an X-axis direction; and the axial direction orthogonal to the Z-axis direction and perpendicular to the floor surface is defined as a Y-axis direction. Although FIG. 1 illustrates more than one gantry apparatus 10 for the sake of convenience in the explanation, the actual configuration of the X-ray CT apparatus 1 includes one gantry apparatus 10.

The gantry apparatus 10 and the couch apparatus 30 are configured to operate on the basis of operations from a user via the console device 40 or operations from the user via an operation unit provided for the gantry apparatus 10 or for the couch apparatus 30. The gantry apparatus 10, the couch apparatus 30, and the console device 40 are communicably connected to one another in a wired or wireless manner.

The gantry apparatus 10 is a device including an imaging system an imaging system configured to radiate X-rays onto a patient P and to acquire projection data from detection data of X-rays that have passed through the patient P. The gantry apparatus 10 includes an X-ray tube 11 (an X-ray generating unit), a filter unit 16, a supporting frame (a filter supporting frame) 160, a wedge, a collimator 17, a photon counting X-ray detector 12, an X-ray high-voltage apparatus 14, a Data Acquisition System (DAS) 18, the rotating frame 13, and a controlling apparatus 15.

The X-ray tube 11 is a vacuum tube configured to generate the X-rays by emitting thermo electrons from a negative pole (a filament) toward a positive pole (a target), with application of high voltage and a supply of a filament current from the X-ray high-voltage apparatus 14. The X-rays are generated as a result of the thermo electrons colliding with the target. The X-rays generated at an X-ray tube focal point of the X-ray tube 11 are formed into a cone beam shape via the collimator 17, for example, so as to be radiated onto the patient P. Examples of the X-ray tube 11 include a rotating anode X-ray tube by which the X-rays are generated as a result of emitting the thermo electrons onto a rotating positive pole (anode).

The photon counting X-ray detector 12 is configured to detect, in units of photons, X-rays that were radiated from the X-ray tube 11 and have passed through the patient P and to output an electrical signal corresponding to the amount of X-rays to the DAS 18. The photon counting X-ray detector 12 includes, for example, a plurality of rows of detecting elements in each of which a plurality of detecting elements are arranged in a channel direction along an arc centered on a focal point of the X-ray tube 11. For example, the photon counting X-ray detector 12 has a structure in which the plurality of rows of detecting elements are arranged in a slice direction (called a row direction).

More specifically, for example, the photon counting X-ray detector 12 is a detector of an indirect conversion type including a grid, a scintillator array, and an optical sensor array. The scintillator array includes a plurality of scintillators. Each of the scintillators includes a scintillator crystal that outputs light having a photon quantity corresponding to the amount of the X-rays that have become incident thereto. The grid is disposed on the surface of the scintillator array positioned on the X-ray incident side and includes an X-ray blocking plate having a function of absorbing scattered X-rays. The optical sensor array includes a plurality of groups of optical sensors. The groups of optical sensors include a plurality of optical sensors. The optical sensors have a function of amplifying light received from the scintillators and converting the amplified light into electric signals. The optical sensors may be, for example, Avalanche Photo-Diodes (APD) or Silicon Photomultipliers (SiPMs). In other words, the optical sensors are configured to receive the light from the scintillators and to output the electrical signals (pulses) corresponding to the X-ray photons that have become incident thereto. The electrical signals output by the detecting elements may be referred to as detection signals. Peak values (voltage) of the electrical signals (the pulses) have correlation with energy values of the X-ray photons. Alternatively, the photon counting X-ray detector 12 may be a detector of a direct conversion type including a semiconductor element configured to convert the incident X-rays into electrical signals. Candidates for the material of the direct conversion type detector include, for example, cadmium telluride (CdTe) and cadmium zinc telluride (CdZnTe).

The rotating frame 13 is configured to support the X-ray tube 11 and the photon counting X-ray detector 12 so as to be rotatable on a rotation axis. More specifically, the rotating frame 13 is an annular frame configured to support the X-ray tube 11 and the photon counting X-ray detector 12 so as to oppose each other and configured to rotate the X-ray tube 11 and the photon counting X-ray detector 12 via the controlling apparatus 15 (explained later). The rotating frame 13 is rotatably supported on a fixed frame formed with metal such as aluminum. More specifically, the rotating frame 13 is connected to an edge part of the fixed frame via a bearing. The rotating frame 13 is configured to rotate on a rotation axis Z at a predetermined angular speed, while receiving motive power from a driving mechanism of the controlling apparatus 15.

In addition to supporting the X-ray tube 11 and the photon counting X-ray detector 12, the rotating frame 13 further includes and supports the X-ray high-voltage apparatus 14 and the DAS 18. The rotating frame 13 structured in this manner is housed in a casing that has a substantially circular cylindrical shape and has formed therein an opening (a bore) 131 serving as an image taking space. The opening 131 substantially matches a field of view (FOV). The central axis of the opening 131 matches the rotation axis Z of the rotating frame 13. In this situation, for example, the detection data generated by the DAS 18 is transmitted from a transmitter including a light emitting diode (LED) to a receiver including a photodiode and being provided in a non-rotation part (e.g., the fixed frame) of the gantry apparatus 10, through optical communication, and is further transferred to the console device 40. The method for transmitting the detection data from the rotating frame 13 to the non-rotation part of the gantry apparatus 10 is not limited to optical communication as mentioned above and may be realized with any of other contactless data transfer methods.

The X-ray high-voltage apparatus 14 includes: a high-voltage generating device including electric circuitry such as a transformer, a rectifier, and the like and having a function of generating the high voltage to be applied to the X-ray tube 11 and the filament current to be supplied to the X-ray tube 11; and an X-ray controlling apparatus configured to control the output voltage in accordance with the X-rays radiated by the X-ray tube 11. The high-voltage generating device may be of a transformer type or of an inverter type. Further, the X-ray high-voltage apparatus 14 may be provided for the rotating frame 13 or may be provided on the side of a fixed frame (not illustrated) of the gantry apparatus 10.

The controlling apparatus 15 includes: processing circuitry having a Central Processing Unit (CPU) or the like; and a driving mechanism configured with a motor, an actuator, and/or the like. As hardware resources, the processing circuitry includes a processor such as a CPU or a Micro Processing Unit (MPU) and a memory such as a Read-Only Memory (ROM) or a Random Access Memory (RAM). Further, the controlling apparatus 15 may be realized by using an Application Specific Integrated Circuit (ASIC), a Field Programmable Gate Array (FPGA), or any of other types of Complex Programmable Logic Devices (CPLDs) and Simple Programmable Logic Devices (SPLDs). According to a command from the console device 40, the controlling apparatus 15 is configured to control the X-ray high-voltage apparatus 14, the DAS 18, and the like. The processor is configured to perform the control by reading and realizing the programs saved in the memory.

Further, the controlling apparatus 15 has a function of receiving an input signal from an input interface attached to the console device 40 or to the gantry apparatus 10 and controlling operations of the gantry apparatus 10 and the couch apparatus 30. For example, the controlling apparatus 15 is configured to exercise control, upon receipt of input signals, to cause the rotating frame 13 to rotate, to cause the gantry apparatus 10 to tilt, and to cause the couch apparatus 30 and the couchtop 33 to operate. In this situation, the control to tilt the gantry apparatus 10 may be realized as a result of the controlling apparatus 15 rotating the rotating frame 13 on an axis parallel to the X-axis direction, according to tilting angle (tilt angle) information input through an input interface attached to the gantry apparatus 10. Further, the controlling apparatus 15 may be provided for the gantry apparatus 10 or for the console device 40. Further, instead of saving the programs in a memory, the controlling apparatus 15 may be configured to directly incorporate the programs in the circuitry of one or more processors. In that situation, the one or more processors realize the abovementioned control by reading and executing the programs incorporated in the circuitry thereof.

The wedge is a filter used for adjusting the X-ray amount of the X-rays radiated from the X-ray tube 11. More specifically, the wedge is a filter configured to pass and attenuate the X-rays radiated from the X-ray tube 11, so that the X-rays radiated from the X-ray tube 11 onto the patient P have a predetermined distribution. For example, the wedge may be a wedge filter or a bow-tie filter and is a filter obtained by processing aluminum so as to have a predetermined target angle and a predetermined thickness. When the filter unit 16 is inserted in a radiation range of the X-rays (hereinafter, "X-ray radiation range") 113, the wedge is caused to retreat from the X-ray radiation range 113 under control of processing circuitry 44.

The filter unit 16 is arranged between the X-ray tube 11 and the photon counting X-ray detector 12. For example, the filter unit 16 is arranged between the couchtop 33 and the X-ray tube 11, the couchtop 33 being arranged between the X-ray tube 11 and the photon counting X-ray detector 12. The filter unit 16 includes a first filter and a second filter.

Figure 2:
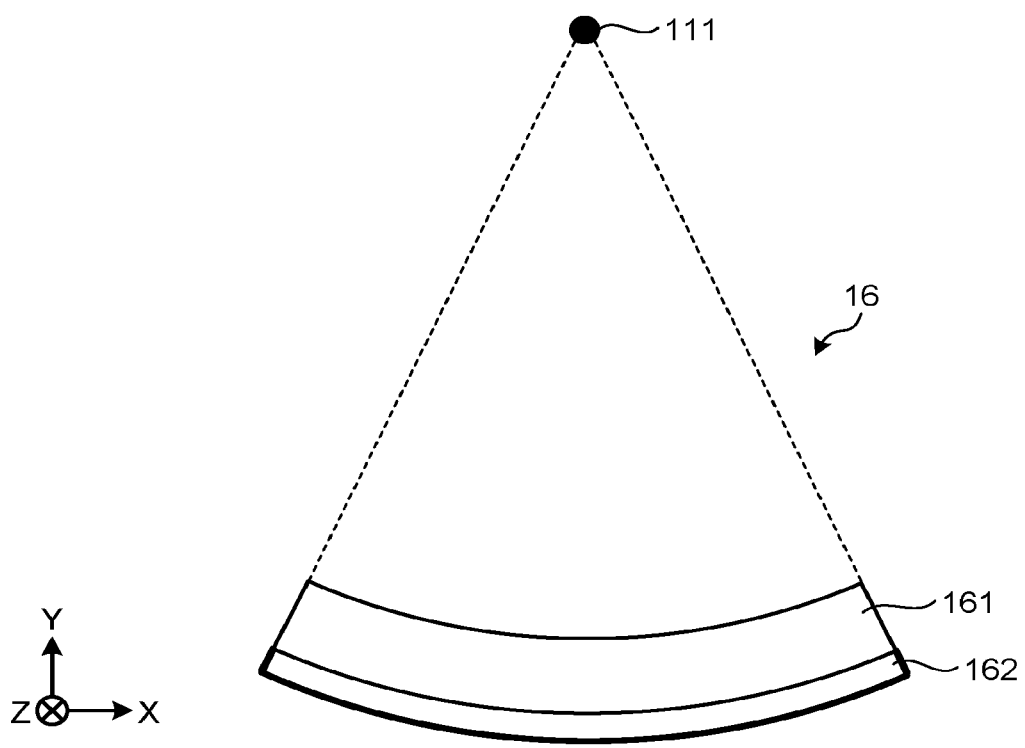
FIG. 2 is a drawing illustrating an example of a cross-section of a filter unit according to the embodiment.

FIG. 2 is a drawing illustrating an example of a cross-section of the filter unit 16. The filter unit 16 has a substantially arc shape centered on an X-ray tube focal point 111. The filter unit 16 has a uniform thickness. In other words, the thickness of the filter unit 16 is uniform on any of the straight lines connecting the X-ray tube focal point 111 to each of the plurality of detecting elements included in the photon counting X-ray detector 12.

A first filter 161 has a substantially arc shape centered on the X-ray tube focal point 111. The first filter 161 has a uniform thickness. In other words, the thickness of the first filter 161 is uniform on any of the straight lines connecting the X-ray tube focal point 111 to each of the plurality of detecting elements included in the photon counting X-ray detector 12. When the filter unit 16 is inserted in the X-ray radiation range 113 generated by the X-ray tube 11, the first filter 161 opposes an X-ray radiation window of the X-ray tube 11. The first filter 161 is configured to shape the spectrum of the X-rays generated at the X-ray tube focal point 111. The first filter 161 is configured with a plurality of types of metal that pass such X-rays that are in an energy region (hereinafter, "high energy region") higher than the energy of the X-ray fluorescence generated by a second filter 162, in the spectrum of the X-rays radiated from the X-ray tube 11.

The first filter 161 is configured with the plurality of types of metal. For example, the first filter 161 is configured so as to include one or both of aluminum and copper. For example, when the first filter 161 is configured with aluminum and copper, the aluminum and the copper have mutually-different and uniform thicknesses. The first filter 161 may be referred to as a shaping filter or a spectrum shaping filter. The X-rays that have passed through the first filter 161 serve as an X-ray source for generating the X-ray fluorescence (monochromatic X-rays) at the second filter 162.

Figure 3:
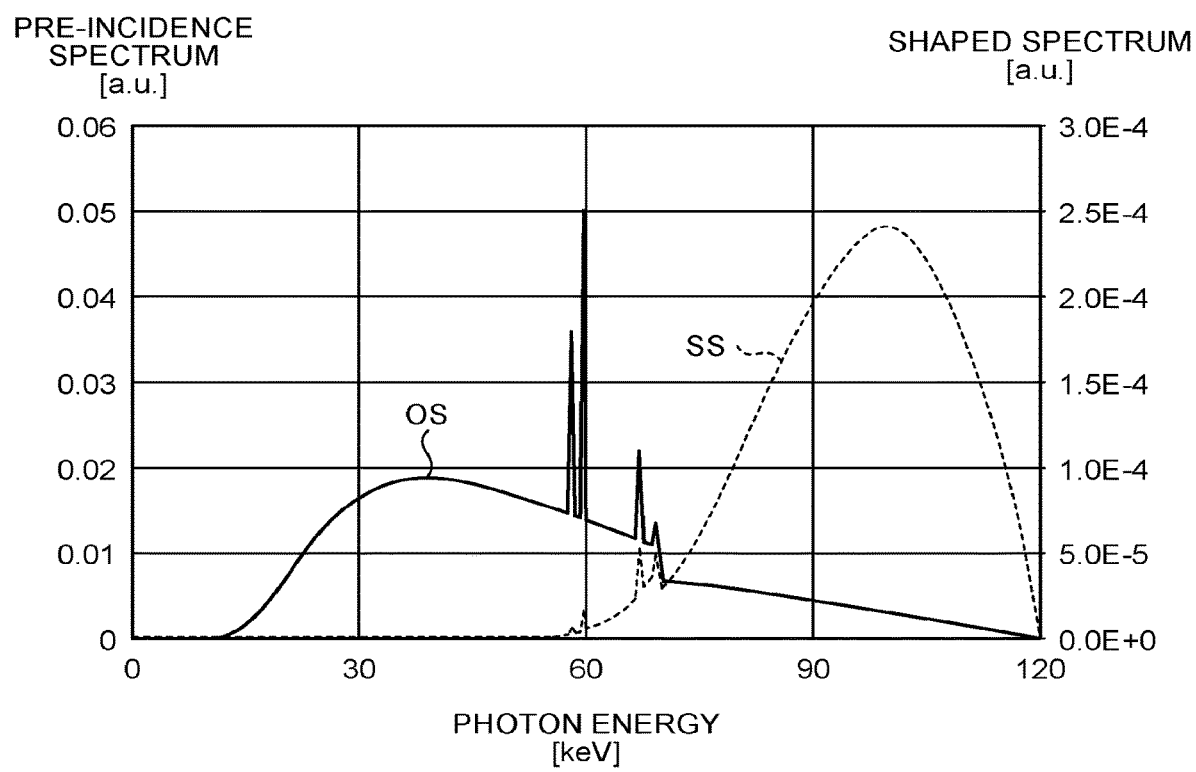
FIG. 3 is a chart according to the embodiment illustrating examples of a pre-incidence spectrum and a shaped spectrum.

FIG. 3 is a chart illustrating, in relation to photon energy, examples of an X-ray spectrum before becoming incident to the first filter 161 (hereinafter "pre-incidence spectrum") OS and an X-ray spectrum that has passed through the first filter 161 (hereinafter "shaped spectrum") SS. The pre-incidence spectrum OS corresponds to the spectrum of the X-rays generated at the X-ray tube focal point 111 of the X-ray tube 11. The shaped spectrum SS corresponds to the spectrum of the X-rays resulting from the first filter 161 shaping the pre-incidence spectrum OS. In FIG. 3, to make it easier to recognize the shaped spectrum SS, the arbitrary units (a. u.) of the shaped spectrum SS are expressed by using order different from that of the arbitrary units of the pre-incidence spectrum OS. As illustrated in FIG. 3, with respect to the X-rays generated by the X-ray tube 11, the first filter 161 is configured to block the X-rays in the region other than the high energy region and to reduce the radiation amount of the X-rays in the high energy region.

The shaped spectrum SS illustrated in FIG. 3 indicates a spectrum observed when, for example, the second filter 162 is configured with a substance (e.g., tin: approximately 25 keV; molybdenum: approximately 20 keV) of which the energy of the K-absorption edge is equal to or smaller than 50 KeV. The thickness of the first filter 161 is set according to the K-absorption edge energy of the substance used for the second filter 162 configured to generate the X-ray fluorescence. When the second filter 162 is configured with tin, the first filter 161 is configured with, for example, aluminum having a thickness of 1 cm and copper having a thickness of 0.5 cm. In this situation, the first filter 161 has a two-layer structure using the aluminum and the copper. Regarding the aluminum and the copper in the two-layer structure, when one of the two is positioned on the X-ray incident side, the other is positioned on the X-ray exit side.

The second filter 162 has a substantially arc shape centered on the X-ray tube focal point 111. The second filter 162 has a uniform thickness. In other words, the thickness of the second filter 162 is uniform on any of the straight lines connecting the X-ray tube focal point 111 to each of the plurality of detecting elements included in the photon counting X-ray detector 12. The second filter 162 is provided on the X-ray exit side of the first filter 161. When the filter unit 16 is inserted in the X-ray radiation range 113, the X-ray exit side of the second filter 162 opposes the photon counting X-ray detector 12. The second filter 162 is configured to generate the X-ray fluorescence on the basis of the X-rays related to the spectrum resulting from the shaping by the first filter 161. The second filter 162 is configured with heavy metal. For example, the second filter 162 is configured with molybdenum, tin, tungsten, or lead. The second filter 162 may be referred to as a heavy metal filter, an X-ray fluorescence generating filter, or a monochromatic X-ray generating filter.

Figure 4:
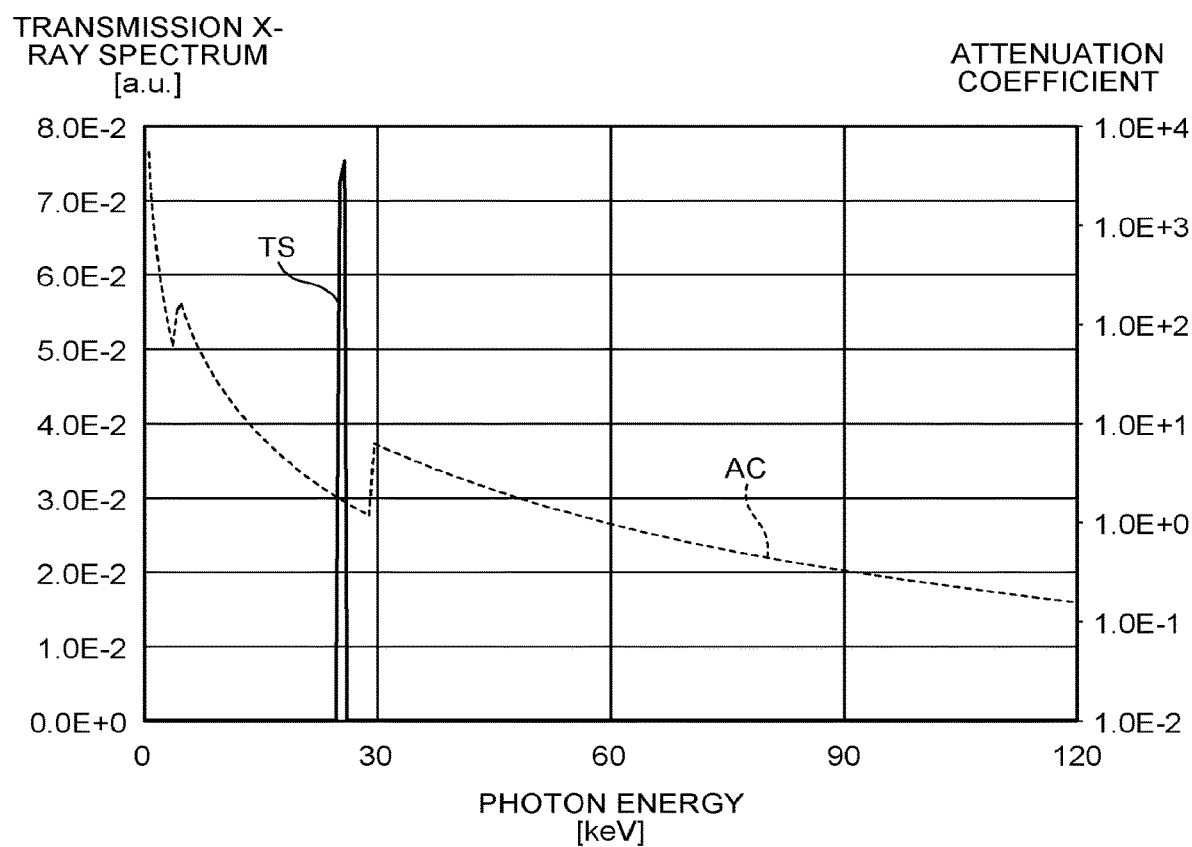
FIG. 4 is a chart according to the embodiment illustrating examples of a transmission X-ray spectrum and a distribution of attenuation coefficients of a second filter.

FIG. 4 is a chart illustrating, in relation to photon energy, examples of a spectrum (hereinafter, "transmission X-ray spectrum TS") of the X-ray fluorescence generated by the second filter 162 and the X-rays that have passed through the second filter 162 and a distribution AC of attenuation coefficients of the second filter 162. As illustrated in FIG. 4, in the transmission X-ray spectrum TS, a sharp peak is exhibited at the K-absorption edge of the heavy metal included in the second filter 162.

Figure 5:
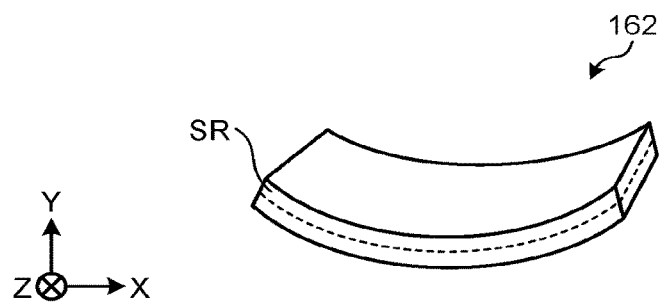
FIG. 5 is a drawing according to the embodiment schematically illustrating a fluorescence position of the second filter.

FIG. 5 is a drawing schematically illustrating a position (hereinafter "fluorescence position") in the second filter 162 in which the X-ray fluorescence is generated. As illustrated in FIG. 5, the X-ray fluorescence is generated in a region SR spanning from the top face of the second filter 162 to the dotted line. When the second filter 162 is configured with tin, the fluorescence position is a position hundreds of micrometers (μm) away from the surface of the second filter 162. In that situation, the energy of the X-ray fluorescence generated by the second filter 162 is approximately 25 keV. When the thickness of the second filter 162 is larger than 300 μm, the second filter 162 attenuates the X-ray fluorescence generated in the fluorescence position. For this reason, when the second filter 162 is configured with tin, it is desirable to arrange the thickness of the second filter 162 to be 0.2 mm or smaller, for example. Further, because the second filter 162 is configured with heavy metal, the second filter 162 reduces such X-rays that have passed through the first filter 161 but do not contribute to the generation of the X-ray fluorescence by the second filter 162. Consequently, in the spectrum of the X-rays that have passed through the second filter 162, the X-ray fluorescence is dominant.

For example, when the second filter 162 is configured with molybdenum, the energy of the X-ray fluorescence generated by the second filter 162 is approximately 20.0 keV. In another example, when the second filter 162 is configured with tungsten, the energy of the X-ray fluorescence generated by the second filter 162 is approximately 58 keV. In yet another example, when the second filter 162 is configured with lead, the energy of the X-ray fluorescence generated by the second filter 162 is approximately 74.0 keV.

Returning to the description of FIG. 1, the supporting frame 160 is configured to support the filter unit 16 so as to be insertable into the X-ray radiation range 113 generated by the X-ray tube 11. Further, the supporting frame 160 is configured to support the wedge so as to be insertable into the X-ray radiation range 113. For example, the supporting frame 160 is configured with a guide including a rail and a block. The supporting frame 160 is provided with a motor 164 configured to operate the block. The motor 164 is driven by the control of the processing circuitry 44. More specifically, under the control exercised by the processing circuitry 44 over the motor 164, the supporting frame 160 is configured to move the filter unit 16 into the X-ray radiation range 113 and to cause the wedge to retreat from the X-ray radiation range 113. Also, under the control exercised by the processing circuitry 44 over the motor 164, the supporting frame 160 is configured to move the wedge into the X-ray radiation range 113 and to cause the filter unit 16 to retreat from the X-ray radiation range 113. In this situation, on the supporting frame 160 two or more wedges and two or more filter units may be installed in accordance with the body thickness of the patient P. Among the plurality of filter units, the thicknesses of the first filters 161 are mutually different, while the materials and the thicknesses of the second filters 162 are mutually different.

Figure 6:
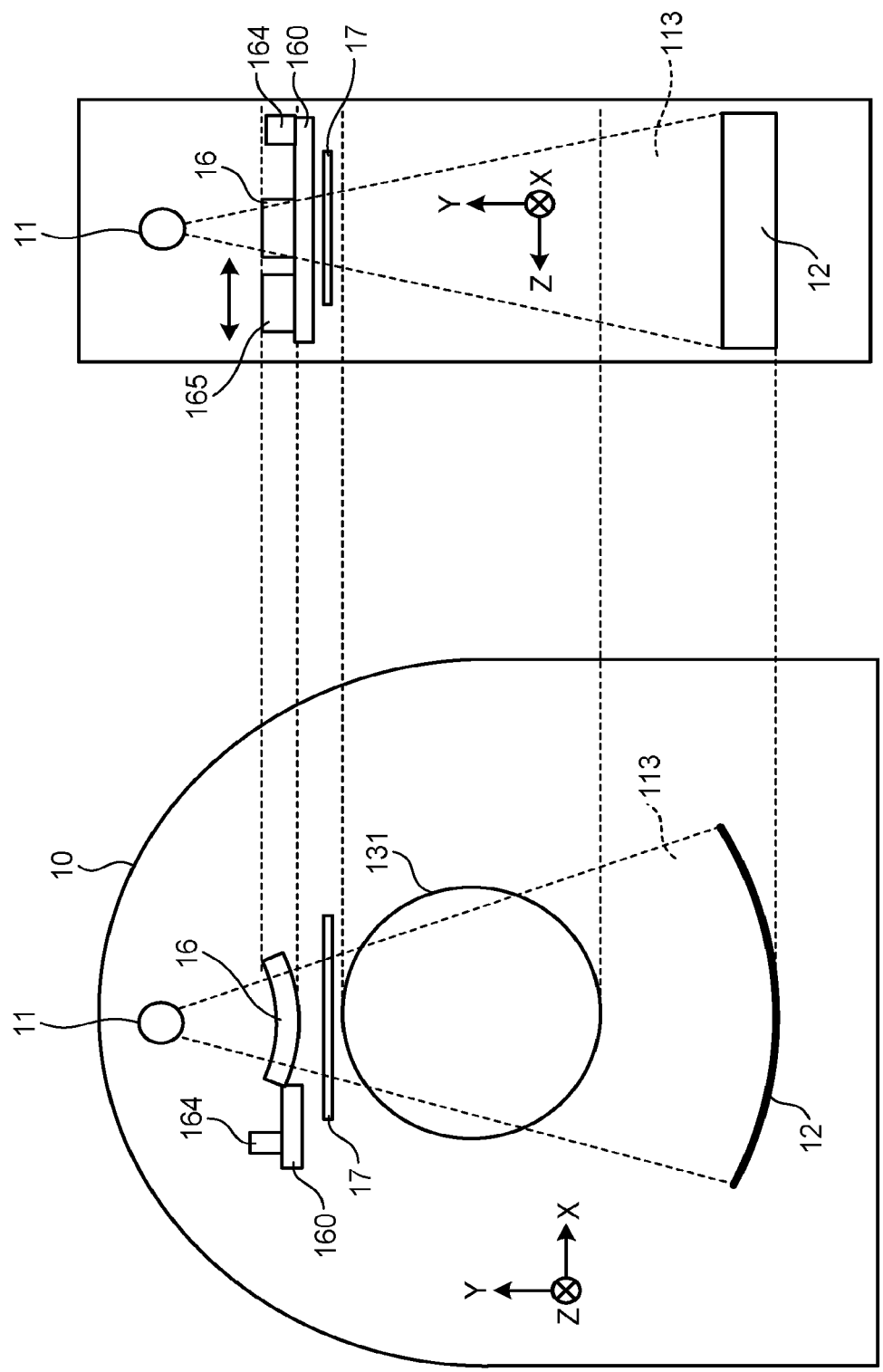
FIG. 6 is a drawing according to the embodiment illustrating an example of a positional relationship among a supporting frame, the filter unit, and a wedge.

FIG. 6 is a drawing illustrating an example of a positional relationship among the supporting frame 160, the filter unit 16, and a wedge 165. The arrow in FIG. 6 indicates moving directions of the wedge 165 and the filter unit 16, when moving into the X-ray radiation range 113 and retreating from the X-ray radiation range 113. When the filter unit 16 is inserted in the X-ray radiation range 113, the filter unit 16 is positioned between the couchtop 33 and the X-ray tube 11.

The collimator 17 is configured with lead plates or the like used for narrowing down the X-rays that have passed through the wedge 165 into the X-ray radiation range 113 and is configured to form a slit with a combination of the plurality of lead plates or the like.

The DAS 18 includes a plurality of counting circuits. Each of the plurality of counting circuits includes: an amplifier configured to perform an amplifying process on the electrical signals output from the detecting elements of the photon counting X-ray detector 12; and an Analog/Digital (A/D) converter configured to convert the amplified electrical signals into digital signals. The DAS 18 is configured to generate the detection data, which is a result of a counting process using the detection signals from the photon counting X-ray detector 12. The result of the counting process is data in which the number of photons in the X-rays is assigned to each energy bin. For example, the DAS 18 is configured to count the photons (X-ray photons) derived from the X-rays that were radiated from the X-ray tube 11 and have passed through the patient P and to obtain the result of the counting process by discriminating energy levels of the counted photons. The detection data generated by the DAS 18 is transferred to the console device 40. The detection data is a set of data made up of: channel numbers and row numbers of detector pixels from which the detection data was generated; view numbers indicating acquired views (which may be called projection angles); and values indicating the radiation amounts of the detected X-rays. As the view numbers, the order (acquisition times) in which the views were acquired may be used. Alternatively, numbers (e.g., 1 to 1000) indicating rotation angles of the X-ray tube 11 may be used. For example, each of the plurality of counting circuits of the DAS 18 is realized with a group of circuits having installed therein circuit elements capable of generating the detection data.

Figure 7:
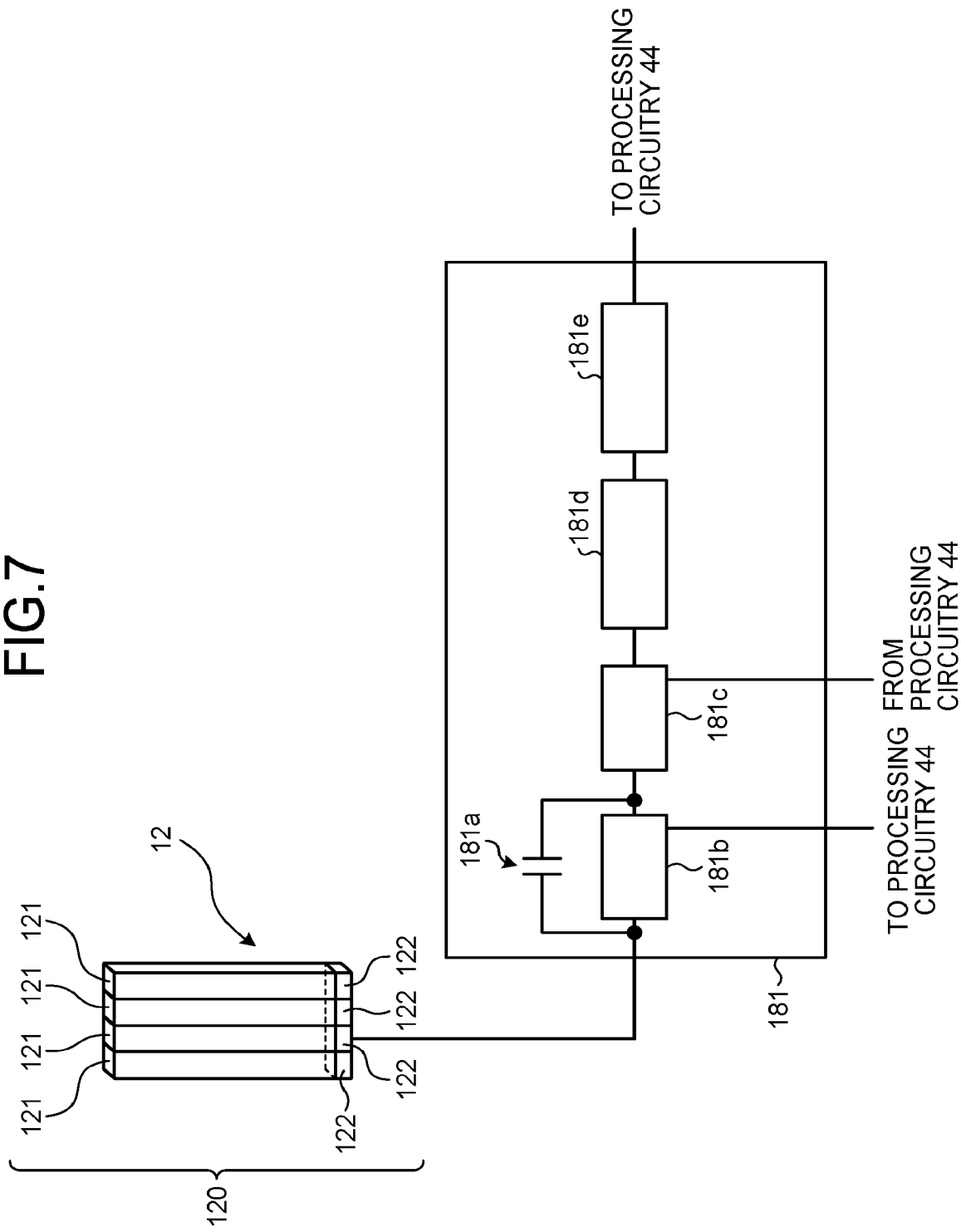
FIG. 7 is diagram for explaining a counting circuit according to the embodiment.

FIG. 7 is a drawing for explaining a counting circuit 181. As illustrated in FIG. 7, the photon counting X-ray detector 12 includes the plurality of detecting elements configured to detect the X-ray photons. The example in FIG. 7 illustrates only four detecting elements 120 among the plurality of detecting elements included in the photon counting X-ray detector 12. As for the detecting elements 120, among the plurality of counting circuits included in the DAS 18, only a counting circuit 181 corresponding to one of the detecting elements 120 is illustrated.

As illustrated in FIG. 7, the detecting elements 120 are indirect conversion type detectors each of which is configured by using a scintillator 121 and a group of optical sensors 122. In other words, the photon counting X-ray detector 12 includes the plurality of detecting elements 120 each of which includes a scintillator 121 and a group of optical sensors 122. The group of optical sensors 122 provided for each of the scintillators 121 structures one pixel. Further, the group of optical sensors 122 is made up of a plurality of optical sensors.

The counting circuit 181 is configured to count the number of X-ray photons that have become incident to the corresponding detecting element 120, by discriminating each of the electric charges output by the detecting element 120. Further, by performing a calculating process based on the magnitude of each of the electric charges, the counting circuit 181 is configured to measure the energy of the counted X-ray photons. For example, the counting circuit 181 includes a capacitor 181a, an amplifying circuit 181b, a waveform shaping circuit 181c, a comparator circuit 181d, and a counter 181e.

The capacitor 181a is configured to store therein each of the electric charges output by the detecting element 120. With respect to a plurality of scintillation light beams generated by one X-ray photon, the output of the capacitor 181a corresponds to multiplexing the outputs of the plurality of optical sensors with one another.

The amplifying circuit 181b is a circuit configured to integrate the electric charges collected by the capacitor 181a in response to the X-ray photons that have become incident to the detecting element 120, and to output the result as a pulse signal of the electric energy. The pulse signal has a peak and an area corresponding to the energy amount of the photons. In other words, the peak value of the electric signal (the pulse) has a correlation with the energy value of the X-ray photons. For example, a peak value A and the energy value E of the X-ray photons have a relation expressed with a linear expression "$A=\alpha \times E+\beta$" (hereinafter, "peak energy relational expression") using a coefficient $\alpha$ and another coefficient $\beta$. In this situation, the coefficient $\alpha$ corresponds to a gain used by the waveform shaping circuit 181c, whereas the coefficient $\beta$ corresponds to an offset used by the waveform shaping circuit 181c.

To the output side of the amplifying circuit 181b, the processing circuitry 44 and the waveform shaping circuit 181c are connected. Under the control of the processing circuitry 44, the amplifying circuit 181b is configured to switch the output destination of the pulse signal between the processing circuitry 44 and the waveform shaping circuit 181c. For example, when a process (hereinafter, "energy calibrating process") related to calibrating the output of the photon counting X-ray detector 12 and the energy of the X-rays that have become incident to the photon counting X-ray detector 12 is to be performed, the amplifying circuit 181b outputs the pulse signal to the processing circuitry 44. In contrast, when X-ray CT image data is to be constructed, the amplifying circuit 181b outputs the pulse signal to the waveform shaping circuit 181c.

The waveform shaping circuit 181c is a circuit configured to shape the waveform of the pulse signal, by adjusting frequency characteristics of the pulse signal output from the amplifying circuit 181b and also applying the gain $\alpha$ and the offset $\beta$. The gain $\alpha$ and the offset $\beta$ used by the waveform shaping circuit 181c are adjusted by a calibrating function 445, on the basis of a result of the energy calibrating process.

The comparator circuit 181d is a circuit configured to compare the peak or the area of the pulse signal responding to the incident photons with a threshold value that is set in advance in correspondence with a plurality of energy bands subject to be discriminated and is configured to further output the result of the comparison with the threshold value to the counter 181e on the subsequent stage.

With respect to each of the corresponding energy bands, the counter 181e is configured to count a discrimination result from the waveform of the response pulse signal and to further output the photon counting result to the processing circuitry 44 as digital data.

Returning to the description of FIG. 1, the couch apparatus 30 is a device on which the patient P to be scanned is placed and which is configured to move the patient P. The couch apparatus 30 includes a base 31, a couch driving device 32, the couchtop 33, and a couchtop supporting frame 34. The base 31 is a casing configured to support the couchtop supporting frame 34 so as to be movable in the vertical directions. The couch driving device 32 is a motor or an actuator configured to move the couchtop 33 on which the patient P is placed, along the long axis directions thereof. The couch driving device 32 is configured to move the couchtop 33 according to the control of the console device 40 or the control of the controlling apparatus 15. The couchtop 33 provided on the top face of the couchtop supporting frame 34 is a board on which the patient P is placed. In addition to the couchtop 33, the couch driving device 32 may move the couchtop supporting frame 34 in the long axis directions of the couchtop 33.

The console device 40 includes a memory 41 (a storage unit), a display 42 (a display unit), an input interface 43 (an input unit), and the processing circuitry 44 (a processing unit). Data communication among the memory 41, the display 42, the input interface 43, and the processing circuitry 44 is performed via a bus.

The memory 41 is a storage device configured to store therein various types of information such as a Hard Disk Drive (HDD), a Solid State Drive (SSD), an integrated circuit storage device, or the like. For example, the memory 41 stores therein the projection data and reconstructed image data. Instead of being an HDD, an SSD, or the like, the memory 41 may be a driving device configured to read and write various type of information from and to: a portable storage medium such as a Compact Disk (CD), a Digital Versatile Disk (DVD), or a flash memory; or a semiconductor memory element such as a Random Access Memory (RAM). Further, the saving region of the memory 41 may be in the X-ray CT apparatus 1 or may be in an external storage device connected via a network. Further, the memory 41 is also configured to store therein a controlling program of the present embodiment.

The display 42 is configured to display various types of information. For example, the display 42 is configured to output a medical image (a CT image) generated by the processing circuitry 44, a Graphical User Interface (GUI) used for receiving various types of operations from an operator, and the like. For example, as the display 42, it is possible to use, as appropriate, a Liquid Crystal Display (LCD) device, a Cathode Ray Tube (CRT) display, an Organic Electroluminescence Display (OELD) device, a plasma display, or any other arbitrary display. Alternatively, the display 42 may be provided for the gantry apparatus 10. Further, the display 42 may be of a desktop type or may be configured by using a tablet terminal or the like capable of wirelessly communicating with the main body of the console device 40.

The input interface 43 is configured to receive the various types of input operations from the operator, to convert the received input operations into electrical signals, and to output the electrical signals to the processing circuitry 44. For example, the input interface 43 is configured to receive, from the operator, an acquisition condition used at the time of acquiring the projection data, a reconstruction condition used at the time of reconstructing the CT image, an image processing condition used at the time of generating a post-processing image from the CT image, and the like. For example, as the input interface 43, it is possible to use, as appropriate, a mouse, a keyboard, a trackball, a switch, a button, a joystick, a touchpad, and/or a touch panel display.

In the present embodiment, the input interface 43 does not necessarily have to include a physical operation component part such as a mouse, a keyboard, a trackball, a switch, a button, a joystick, a touchpad, a touch panel display, and/or the like. For instance, possible examples of the input interface 43 include an electrical signal processing circuit configured to receive an electrical signal corresponding to an input operation from an external input device provided separately from the device and to output the received electrical signal to the processing circuitry 44. Further, the input interface 43 is an example of an input unit. Alternatively, the input interface 43 may be provided for the gantry apparatus 10. In another example, the input interface 43 may be configured by using a tablet terminal or the like capable of wirelessly communicating with the main body of the console device 40.

The processing circuitry 44 is configured to control operations of the entirety of the X-ray CT apparatus 1, in accordance with the electrical signals corresponding to the input operations output from the input interface 43. For example, as hardware resources, the processing circuitry 44 includes a processor such as a CPU, an MPU, or a Graphic Processing Unit (GPU) and a memory such as a ROM or a RAM. By employing the processor configured to execute programs loaded into the memory, the processing circuitry 44 executes a system controlling function 441 (a system controlling unit), a pre-processing function 442, a reconstruction processing function 443 (a reconstructing unit), a moving controlling function 444 (a moving controlling unit), and the calibrating function 445 (a calibrating unit). In this situation, the functions 441 to 445 do not necessarily have to be realized by the single processing circuit. Another arrangement is also acceptable in which a processing circuit is structured by combining together a plurality of independent processors, so that the functions 441 to 445 are realized as a result of the processors executing the programs.

On the basis of the input operations received from the operator via the input interface 43, the system controlling function 441 is configured to control the functions of the processing circuitry 44. More specifically, the system controlling function 441 is configured to read the controlling program stored in the memory 41, to load the read controlling program into a memory within the processing circuitry 44, and to control functional units of the X-ray CT apparatus 1 according to the loaded controlling program. For example, on the basis of the input operations received from the operator via the input interface 43, the processing circuitry 44 is configured to control the functions of the processing circuitry 44.

The pre-processing function 442 is configured to generate data obtained by performing a pre-processing process such as a logarithmic converting process, an offset correcting process, an inter-channel sensitivity correcting process, a beam hardening correction, and/or the like, on the detection data output from the DAS 18. The data before the pre-processing process may be referred to as raw data, whereas the data after the pre-processing process may be referred to as projection data.

The reconstruction processing function 443 is configured to generate the CT image data by performing a reconstructing process using a Filtered Back Projection (FBP) method, a successive approximation reconstruction method, or the like, on the projection data generated by the pre-processing function 442. The reconstruction processing function 443 is configured to store the reconstructed CT image data into the memory 41. The projection data generated from the counting result obtained from a photon counting CT process contains information about the energy of the X-rays that were attenuated as a result of passing through the patient P. Accordingly, for example, the reconstruction processing function 443 is capable of reconstructing X-ray CT image data corresponding to a specific energy component. Further, for example, the reconstruction processing function 443 is capable of reconstructing X-ray CT image data corresponding to each of a plurality of energy components.

Further, for example, the reconstruction processing function 443 is capable of assigning a color tone corresponding to an energy component to each of the pixels of the X-ray CT image data corresponding to the various energy components and further generating image data on which a plurality of pieces of X-ray CT image data that are colored in correspondence with the energy components are superimposed. Further, for example, the reconstruction processing function 443 is capable of generating image data that makes it possible to identify substances by using the K-absorption edges unique to the substances. Other examples of the image data generated by the reconstruction processing function 443 include monochromatic X-ray image data, density image data, and effective atomic number image data.

The moving controlling function 444 is configured to control the motor 164 provided for the supporting frame 160, in response to an input operation received from the operator via the input interface 43 or at a predetermined time. The input operation is an input instructing that the energy calibrating process be executed. The predetermined time is, for example, a time during such a period of the day (e.g., in the middle of the night or early in the morning) when no medical examinations are performed by using the X-ray CT apparatus 1. Thus, the moving controlling function 444 is configured to control the moving of the wedge 165 to the outside of the X-ray radiation range 113 and the moving of the filter unit 16 into the X-ray radiation range 113. Further, in response to an instruction to end the energy calibrating process or to start a scan on the patient P, the wedge 165 is inserted into the X-ray radiation range 113, whereas the filter unit 16 is moved to the outside of the X-ray radiation range 113, under the control exercised by the moving controlling function 444 over the motor 164.

The calibrating function 445 is configured to calibrate the outputs of the plurality of detecting elements included in the photon counting X-ray detector 12, on the basis of the X-ray fluorescence generated by the second filter 162. The calibrating function 445 is configured to perform the energy calibrating process on the output of each of the plurality of detecting elements. As a result, the outputs of the plurality of detecting elements are brought into correspondence with energy levels of the X-rays. A procedure in the energy calibrating processing will be explained later. The energy calibrating process Next, the energy calibrating process performed by the X-ray CT apparatus 1 according to the embodiment will be explained. The energy calibrating process corresponds to a calibrating process performed on energy values of the photons measured by the photon counting X-ray detector 12. The energy calibrating process is performed for the purpose of accurately counting the photons for each of the energy levels, by using the photon counting X-ray detector 12 configured as described above. The energy calibrating process according to the present embodiment is generating X-ray fluorescence that is nearly monochrome, by using the X-rays generated by the X-ray tube 11 and obtaining a correspondence relationship between the photon detection values (i.e., the peak values) and the energy values, while using the generated X-ray fluorescence.

Figure 8:
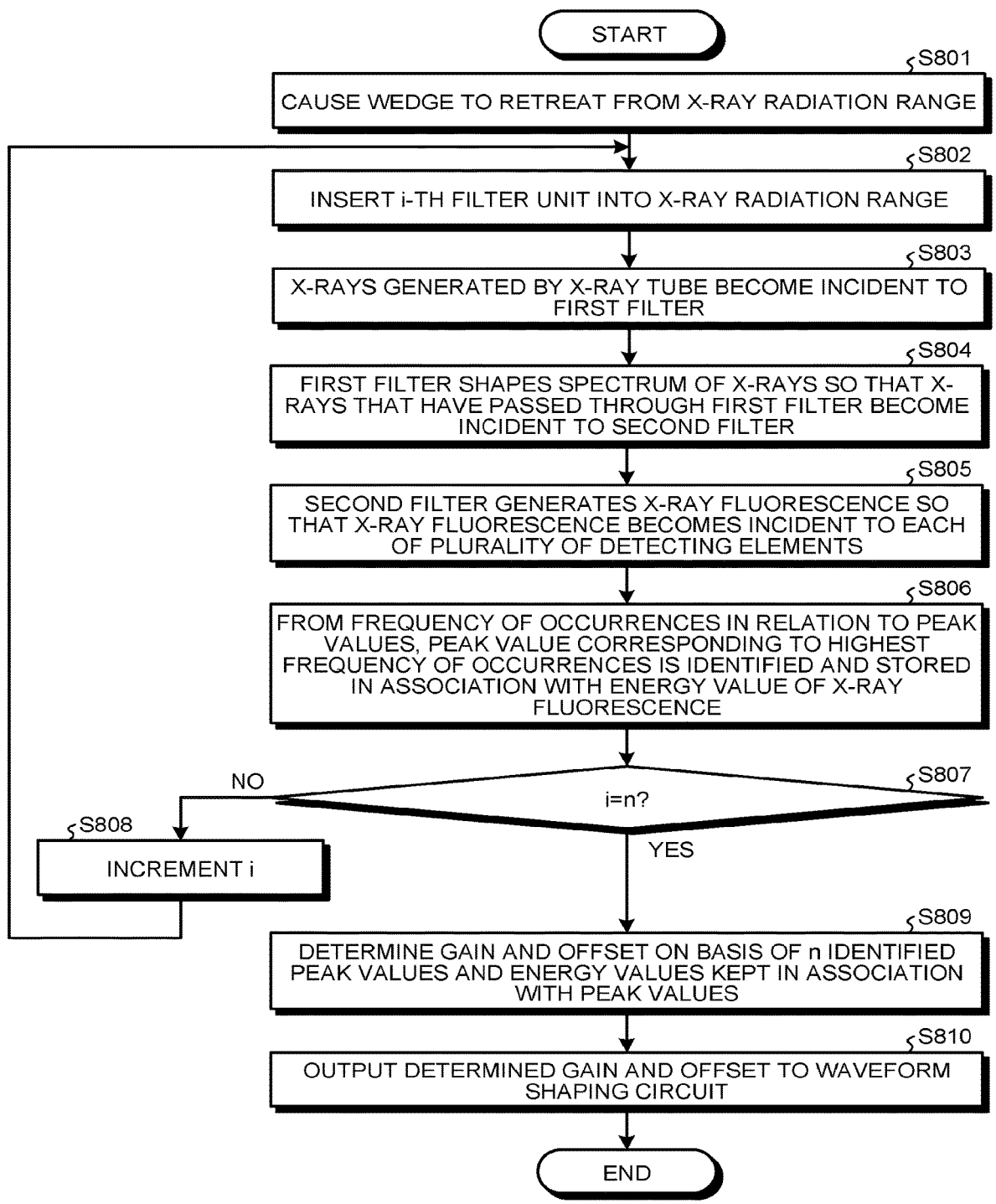
FIG. 8 is a chart illustrating an example of an operation procedure in an energy calibrating process according to the embodiment.

FIG. 8 is a chart illustrating an example of an operation procedure in the energy calibrating process. In the following sections, to explain a specific example, it is assumed that the supporting frame 160 has installed thereon three types of filter units (first, second, and third filter units). In other words, three types of filter units 16 are installed on the supporting frame 160. The three types of filter units are interchangeable in accordance with a targeted energy level. For example, among the three types of filter units, tin is used in the second filter 162 of the first filter unit. Further, among the three types of filter units, tungsten is used in the second filter 162 of the second filter unit. Also, among the three types of filter units, lead is used in the second filter 162 of the third filter unit.

For the sake of convenience in the explanation, a natural number i shall be used for discriminating the plurality of filter units. As stated earlier, the natural number i corresponds to 1, 2, and 3. Prior to the process at step S801, the natural number i is set to 1. During the operation procedure of the energy calibrating process, the natural number i is incremented as appropriate. Further, for the sake of convenience in the explanation, a natural number n shall be used for indicating the total number of filter units. As stated earlier, the natural number n is equal to 3.

Step S801:

In response to an input of an instruction via the input interface 43 that the energy calibrating process be executed or at the predetermined time, the motor 164 is driven by the moving controlling function 444. As a result of the motor 164 being driven, the wedge 165 is caused to retreat from the X-ray radiation range 113, via the supporting frame 160.

Step S802:

As a result of the motor 164 being driven by the moving controlling function 444, the i-th filter unit is inserted in the X-ray radiation range 113 via the supporting frame 160.

Step S803:

Under the control exercised by the controlling apparatus 15 over the X-ray high-voltage apparatus 14, the X-ray tube 11 generates X-rays. The generated X-rays become incident to the first filter 161 of the i-th filter unit, while having the pre-incidence spectrum OS.

Step S804:

The first filter 161 shapes the pre-incidence spectrum OS into the shaped spectrum SS. The X-rays in the high energy region that have passed through the first filter 161 become incident to the second filter 162.

Step S805:

From the X-rays in the high energy region, the second filter 162 generates X-ray fluorescence. Further, of the X-rays in the high energy region, the second filter 162 reduces such X-rays that do not contribute the generation of the X-ray fluorescence by the second filter 162. More specifically, the X-rays in the high energy region repels the electrons in the K-shell of the substance structuring the second filter 162, to an empty orbital of an outer shell. As a result, K-absorption is caused by the X-rays in the high energy region, so that a vacancy is created in the K-shell. As a result of the electrons in the L-shell of the substance structuring the second filter 162 filling the vacancy in the K-shell, X-ray fluorescence having energy equal to the energy difference between the L-shell and the K-shell is generated. The generated X-ray fluorescence becomes incident to each of the plurality of detecting elements included in the photon counting X-ray detector 12.

At step S802, when the first filter unit is inserted in the X-ray radiation range 113, the energy spectrum of the X-ray fluorescence generated at this step exhibits a peak at 25 keV. In another example, at step S802, when the second filter unit is inserted in the X-ray radiation range 113, the energy spectrum of the X-ray fluorescence generated at this step exhibits an X-ray intensity having a peak at 58 keV. In yet another example, at step S802, when the third filter unit is inserted in the X-ray radiation range 113, the energy spectrum of the X-ray fluorescence generated at this step exhibits an X-ray intensity having a peak at 74 keV.

Figure 9:
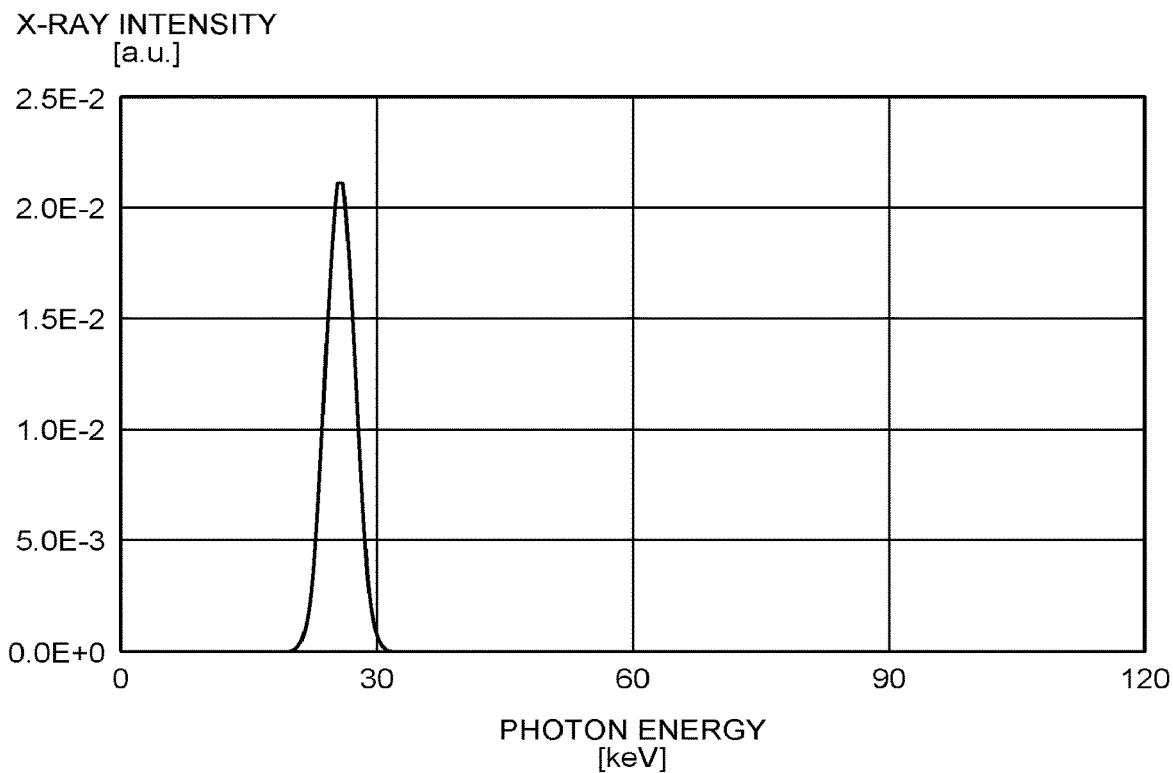
FIG. 9 is a chart according to the embodiment illustrating an example of an energy spectrum of X-ray fluorescence emitted from a first filter unit in which tin is used as the second filter.

FIG. 9 is a chart illustrating an example of an energy spectrum of the X-ray fluorescence emitted from the first filter unit in which tin is used as the second filter 162. The horizontal axis in FIG. 9 expresses photon energy, whereas the vertical axis in FIG. 9 expresses X-ray intensity. As illustrated in FIG. 9, in comparison to the pre-incidence spectrum OS, X-ray fluorescence corresponding to the K-absorption edge of tin is generated efficiently.

Step S806:

Each of the detecting elements 120 detects the X-ray fluorescence as a plurality of X-ray photons. Under the control of the calibrating function 445, the amplifying circuit 181b outputs a plurality of pulse signals corresponding to the plurality of X-ray photons to the processing circuitry 44. The calibrating function 445 detects a peak value of each of the plurality of pulse signals. From the X-ray photon count values (hereinafter, frequency of occurrences) in relation to the detected peak values, the calibrating function 445 identifies a peak value corresponding to the highest frequency of occurrences. The calibrating function 445 stores the identified peak value into the memory 41 so as to be kept in association with the energy of the K-absorption edge of the substance structuring the second filter of the i-th filter unit, i.e., the energy value of the X-ray fluorescence generated at step S805.

Figure 10:
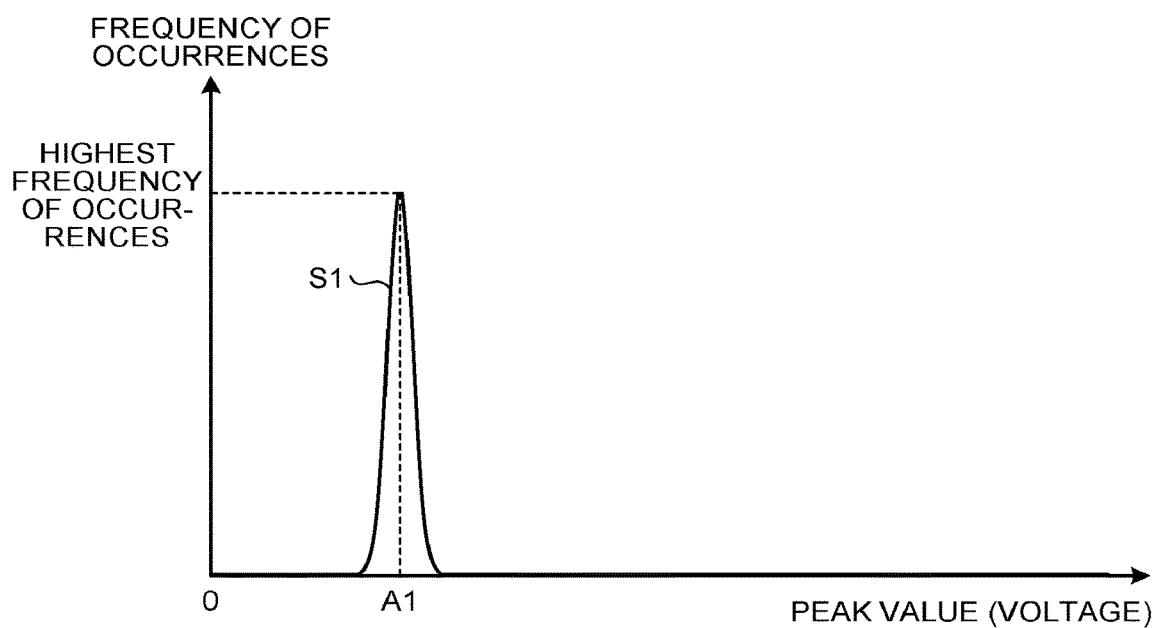
FIG. 10 is a chart according to the embodiment illustrating an example of a histogram indicating, with respect to a detection element, a distribution of frequency of occurrences in relation to peak values.

FIG. 10 is a chart illustrating an example of a histogram S1 indicating, with respect to a detection element, a distribution of X-ray photon count values in relation to peak values, regarding the detection of the X-ray fluorescence generated by the first filter unit. The horizontal axis in FIG.

10 expresses peak values. In FIG. 10, A1 denotes a first peak value corresponding to the highest frequency of occurrences. When the first filter unit is inserted in the X-ray radiation range 113, the calibrating function 445 identifies the first peak value A1. The first peak value A1 corresponds to an energy value E1 (25 keV) of the K-absorption edge related to tin.

Figure 11:
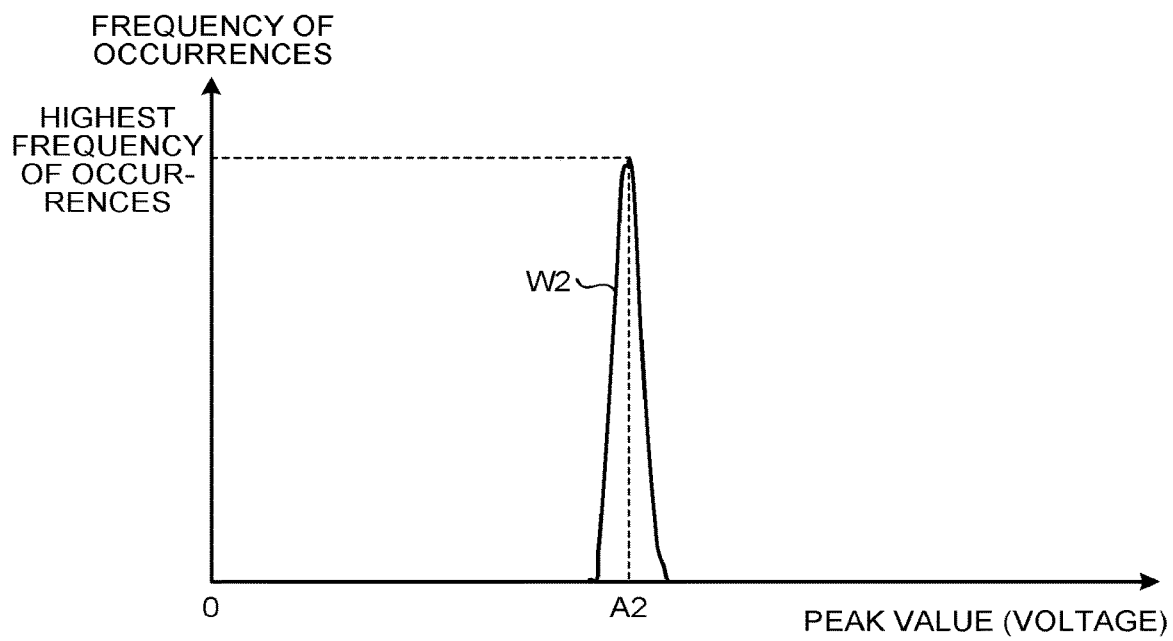
FIG. 11 is a chart according to the embodiment illustrating another example of a histogram indicating, with respect to a detection element, a distribution of frequency of occurrences in relation to peak values.

FIG. 11 is a chart illustrating an example of a histogram W2 indicating, with respect to a detection element, a distribution of frequency of occurrences in relation to peak values, regarding the detection of the X-ray fluorescence generated by the second filter unit. The horizontal axis in FIG. 11 expresses peak values. The vertical axis in FIG. 11 expresses the frequency of occurrences. In FIG. 11, A2 denotes a second peak value corresponding to the highest frequency of occurrences. When the second filter unit is inserted in the X-ray radiation range 113, the calibrating function 445 identifies the second peak value A2. The second peak value A2 corresponds to an energy value E2 (58 keV) of the K-absorption edge related to tungsten.

Figure 12:
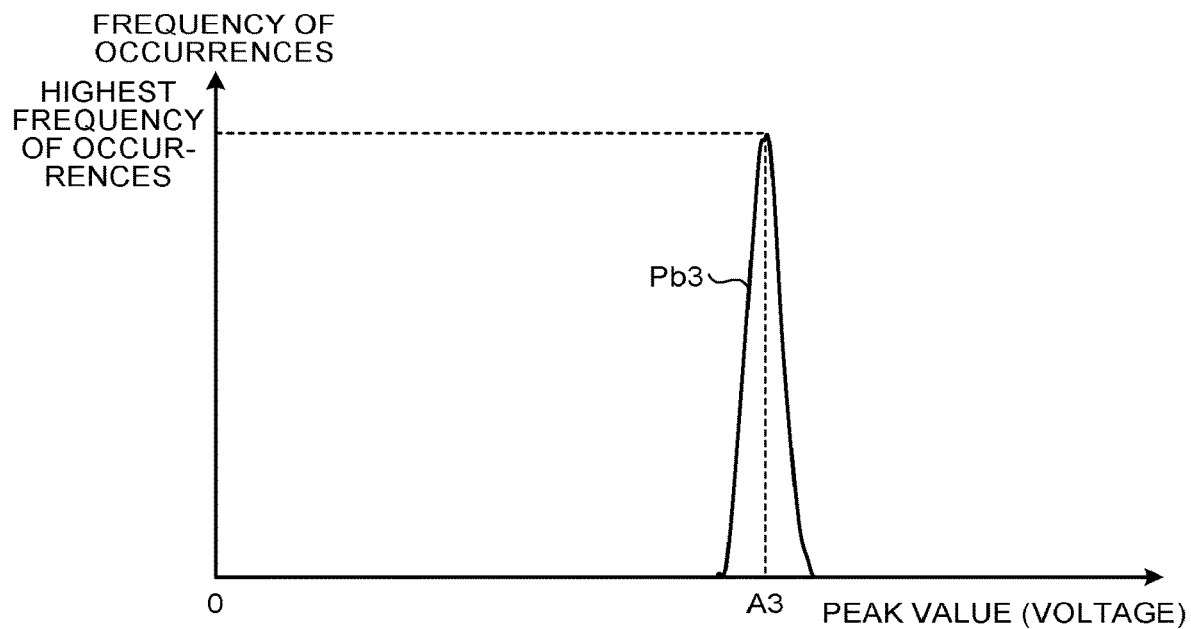
FIG. 12 is a chart according to the embodiment illustrating yet another example of a histogram indicating, with respect to a detection element, a distribution of frequency of occurrences in relation to peak values.
Figure 13:
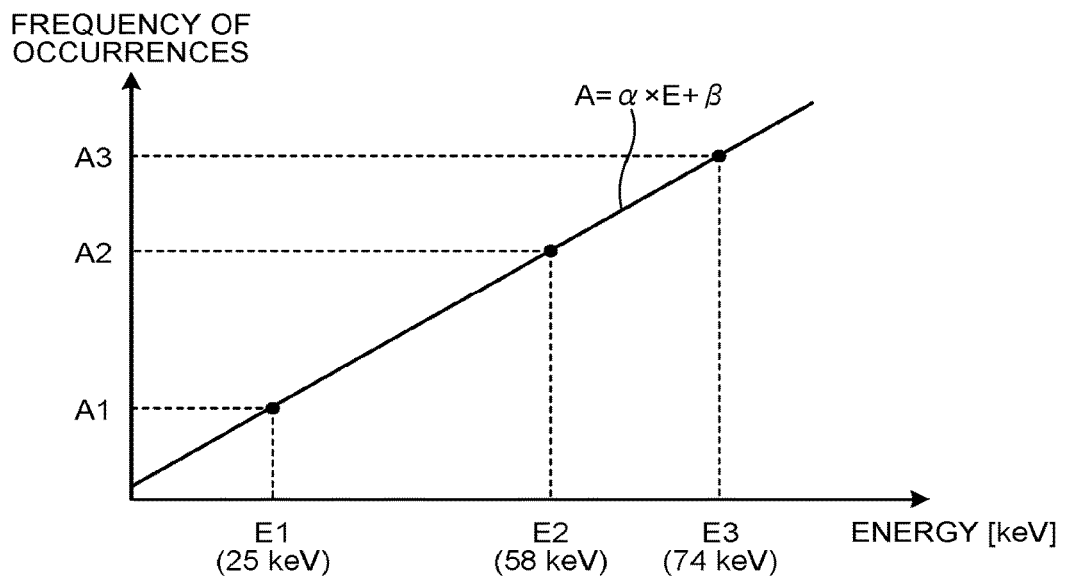
FIG. 13 is a chart according to the embodiment illustrating examples of first to third peak values, a plurality of energy values corresponding to these peak values, and a post-fitting linear expression.

FIG. 12 is a chart illustrating an example of a histogram Pb3 indicating, with respect to a detection element, a distribution of frequency of occurrences in relation to peak values, regarding the detection of the X-ray fluorescence generated by the third filter unit. The horizontal axis in FIG. 12 expresses peak values. The vertical axis in FIG. 12 expresses the frequency of occurrences. In FIG. 13, A3 denotes a third peak value corresponding to the highest frequency of occurrences. When the third filter unit is inserted in the X-ray radiation range 113, the calibrating function 445 identifies the third peak value A3. The third peak value A3 corresponds to an energy value E3 (74 keV) of the K-absorption edge related to lead.

Step S807:

When the natural number i for discriminating the filter units 16 is not equal to the natural number n indicating the total number of filter units 16 (step S807: No), the process at step S808 is performed. When the natural number i is equal to the natural number n (step S807: Yes), the process at step S809 is performed.

Step S808

The natural number i is incremented. Subsequently, the processes at steps S802 through S807 are performed.

Step S809

The calibrating function 445 determines the gain $\alpha$ and the offset $\beta$ used by the waveform shaping circuit 181c, on the basis of the plurality of peak values identified in correspondence with the total number of filter units and the plurality of energy values kept in association with the identified plurality of peak values. More specifically, the calibrating function 445 determines the parameters (i.e., the gain $\alpha$ and the offset $\beta$) in the peak energy relational expression "$A=\alpha \times E+\beta$", by fitting the linear expression using the first to the third peak values and the plurality of energy values at the K-absorption edge corresponding to the peak values.

FIG. 13 is a chart illustrating examples of the first peak value A1, the second peak value A2, the third peak value A3, the plurality of energy values (E1, E2, and E3) corresponding to these peak values, and the post-fitting linear expression. The horizontal axis in FIG. 13 expresses energy, whereas the vertical axis in FIG. 13 expresses peak values. As illustrated in FIG. 13, the calibrating function 445 determines the gain $\alpha$ and the offset $\beta$ by performing the fitting process on the three points (A1,E1), (A2,E2), and (A3,E3).

Step S810:

The processing circuitry 44 outputs the gain $\alpha$ and the offset $\beta$ determined by the calibrating function 445 to the waveform shaping circuit 181c. With the present step, the energy calibrating process ends. At the end of the energy calibrating process or before a scan is performed on the patient P, the supporting frame 160 causes, under the control exercised by the processing circuitry 44 over the motor 164, the filter unit 16 to retreat from the X-ray radiation range 113 and the wedge 165 to be inserted into the X-ray radiation range 113.

The X-ray CT apparatus 1 according to the embodiment described above includes: the X-ray tube 11 configured to generate the X-rays, the photon counting X-ray detector 12 configured to count the photons contained in the X-rays; and the filter unit 16 provided between the X-ray tube 11 and the photon counting X-ray detector 12. The filter unit 16 includes the first filter 161 configured to shape the spectrum of the X-rays; and the second filter 162 configured to generate the X-ray fluorescence, on the basis of the X-rays related to the spectrum resulting from the shaping by the first filter 161.

At the time of performing the energy calibrating process, the filter unit 16 is arranged between the X-ray tube 11 and the couchtop 33, while the first filter 161 configured with one or both of aluminum and copper is configured to block, with respect to the X-rays generated by the X-ray tube 11, the X-rays in the region other than the high energy region and to reduce the radiation amount of the X-rays in the high energy region while passing the X-rays in the high energy region. In addition, the second filter 162 configured with heavy metal such as molybdenum, tin, tungsten, or lead is configured to reduce such X-rays that have passed through the first filter 161 but do not contribute to the generation of the X-ray fluorescence by the second filter 162. With these arrangements, according to the present embodiment, the X-ray fluorescence is dominant in the spectrum of the X-rays that have passed through the second filter 162. It is therefore possible to efficiently generate the monochromatic X-rays.

Figure 14:
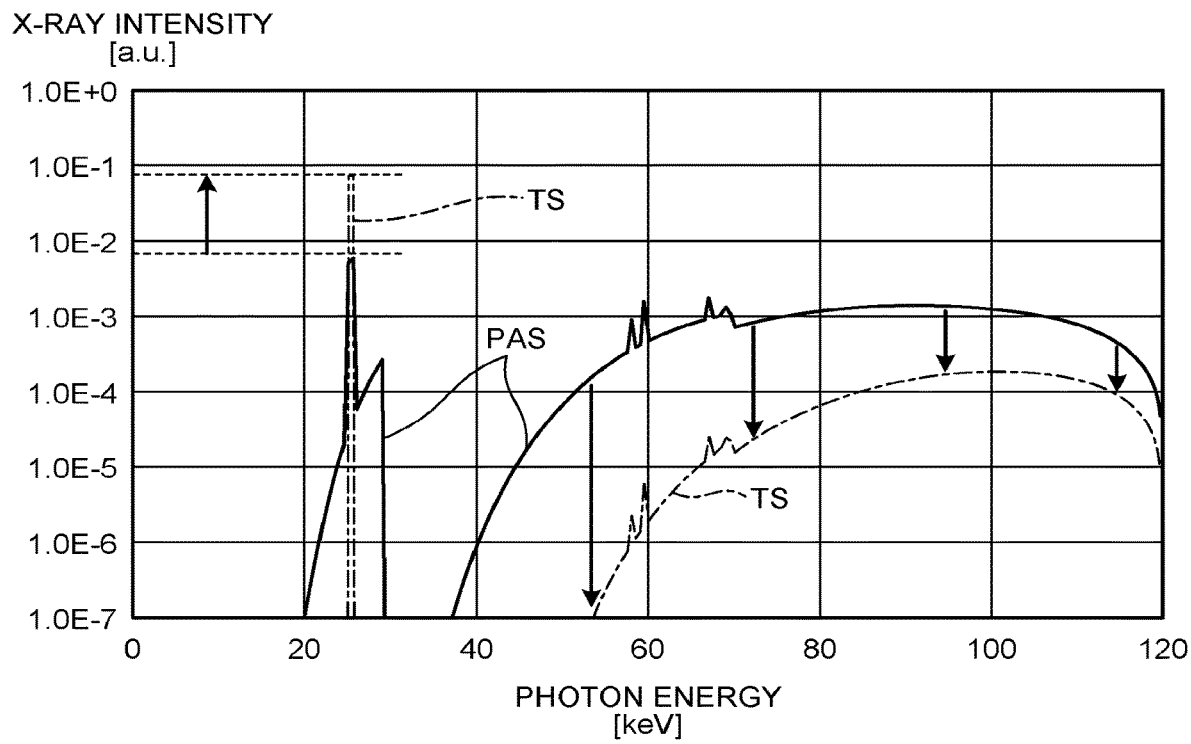
FIG. 14 is a chart illustrating a comparison between a transmission X-ray spectrum according to the embodiment and a spectrum of X-ray fluorescence generated by using a conventional method.

FIG. 14 is a chart illustrating a comparison between the transmission X-ray spectrum TS according to the embodiment and a spectrum PAS of X-ray fluorescence generated by using a conventional method. As illustrated in FIG. 14, the intensity of the X-ray fluorescence generated by the second filter 162 increases approximately ten times higher than the intensity of the X-ray fluorescence indicated with the spectrum PAS of the X-ray fluorescence. In addition, the radiation amount of the X-rays derived from the X-ray tube 11 that have passed through the second filter 162 related to the generation of the X-ray fluorescence in the present embodiment decreases to a level equal to or smaller than one tenth of the level in the conventional example.

Further, in the present embodiment, on the basis of the generated X-ray fluorescence, it is possible to calibrate the outputs of the plurality of detecting elements included in the photon counting X-ray detector 12. In other words, by performing the energy calibrating process using the X-ray fluorescence, which are the monochromatic X-rays of which the energy is known, it is possible to accurately perform the energy calibration.

Further, the X-ray CT apparatus 1 according to the present embodiment further includes: the supporting frame 160 configured to support the filter unit 16 so as to be insertable into the X-ray radiation range 113; and the moving controlling function 444 configured to control the moving of the wedge 165 to the outside of the X-ray radiation range 113 and the moving of the filter unit 16 into the X-ray radiation range 113. With these arrangements, when the energy calibrating process is performed, it is possible to move the wedge 165 to the outside of the X-ray radiation range 113 and to insert the filter unit 16 into the X-ray radiation range 113 easily. Accordingly, it is possible to reduce the burden on the user in the energy calibrating process and to improve efficiency of the energy calibrating process.

Figure 15:
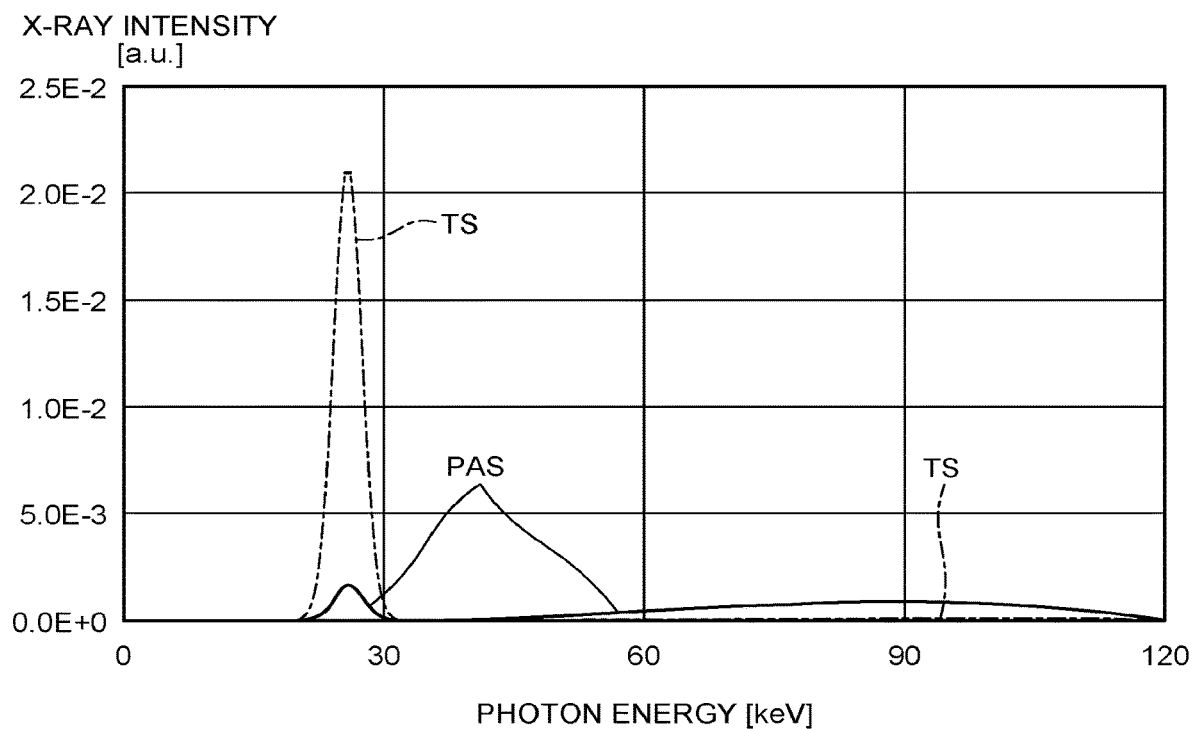
FIG. 15 is a chart for explaining advantageous effects exhibited when the thickness of the second filter according to the embodiment is reduced.
Figure 16:
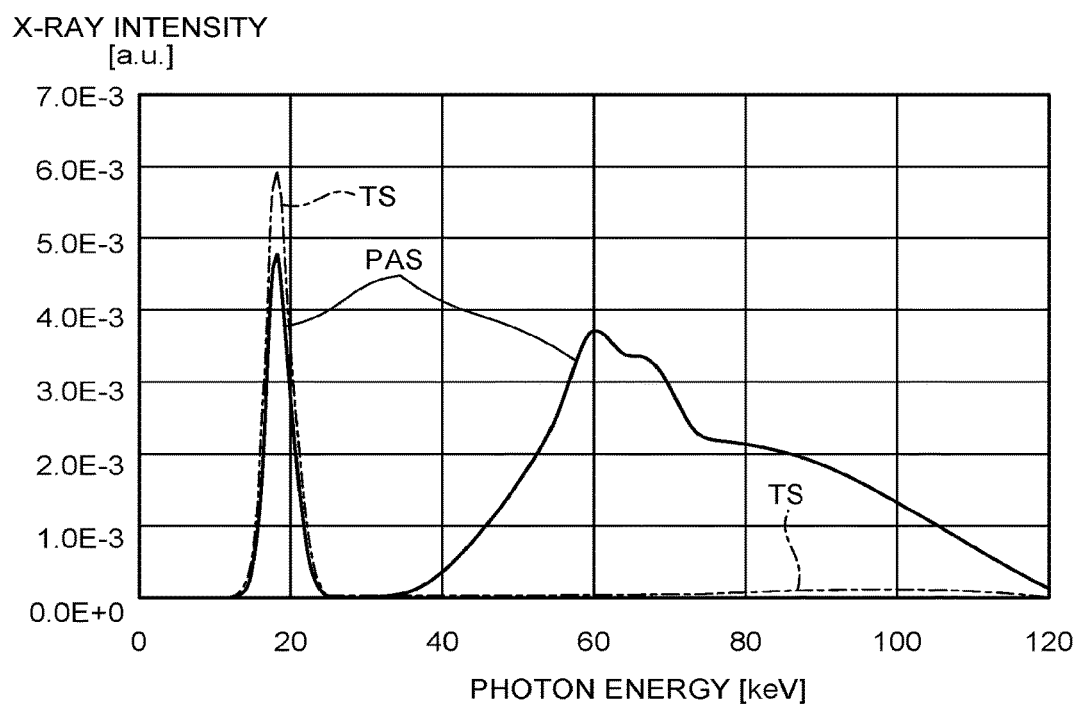
FIG. 16 is another chart for explaining the advantageous effects exhibited when the thickness of the second filter according to the embodiment is reduced.
Figure 17:
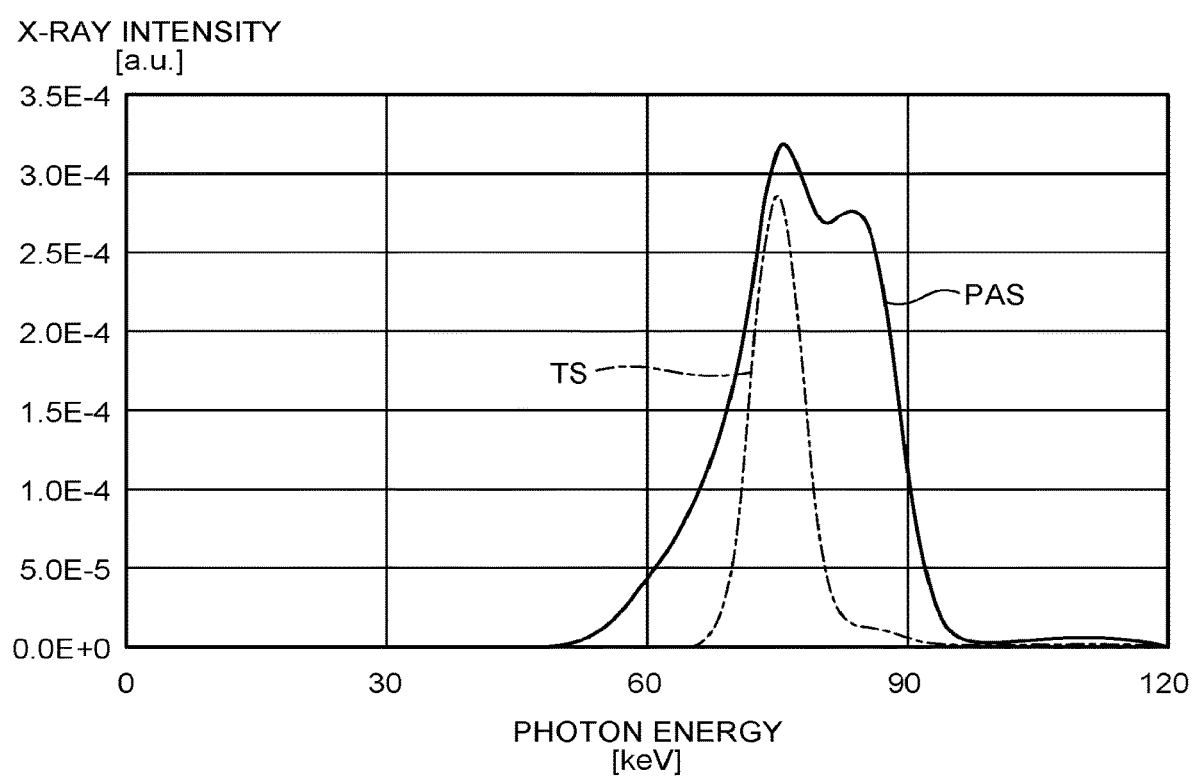
FIG. 17 is yet another chart for explaining the advantageous effects exhibited when the thickness of the second filter according to the embodiment is reduced.

Furthermore, even when the thickness of the second filter 162 according to the present embodiment is smaller than that in conventional examples, it is possible to efficiently extract the monochromatic X-rays. This advantageous effect will be explained, with reference to FIGS. 15 to 17. FIG. 15 is a chart illustrating a comparison between a transmission X-ray spectrum TS observed when using the second filter 162 configured with tin having a thickness of 200 μm and an X-ray fluorescence spectrum PAS generated by a conventional method using tin having a thickness of 700 μm as a filter. FIG. 16 is a chart illustrating a comparison between a transmission X-ray spectrum TS observed when using the second filter 162 configured with molybdenum having a thickness of 200 μm and an X-ray fluorescence spectrum PAS generated by a conventional method using molybdenum having a thickness of 300 μm as a filter. FIG. 17 is a chart illustrating a comparison between a transmission X-ray spectrum TS observed when using the second filter 162 configured with lead having a thickness of 800 μm and an X-ray fluorescence spectrum PAS generated by a conventional method using lead having a thickness of 1,000 μm as a filter. As illustrated in FIGS. 15 to 17, even when the thicknesses of the second filters 162 are smaller than those in the conventional examples, it is possible to efficiently extract the monochromatic X-rays. Accordingly, in the present embodiment, even when the thickness of the second filter 162 is smaller than that in the conventional examples, the X-ray fluorescence is dominant, and it is therefore possible to efficiently generate the monochromatic X-rays.

A Modification Example

In the present modification example, the filter unit 16 is arranged between the couchtop 33 and the photon counting X-ray detector 12. An X-ray CT apparatus according to the present modification example further includes a wedge supporting frame configured to support the wedge 165. The supporting frame 160 according to the present modification example is configured to support the filter unit 16.

Figure 18:
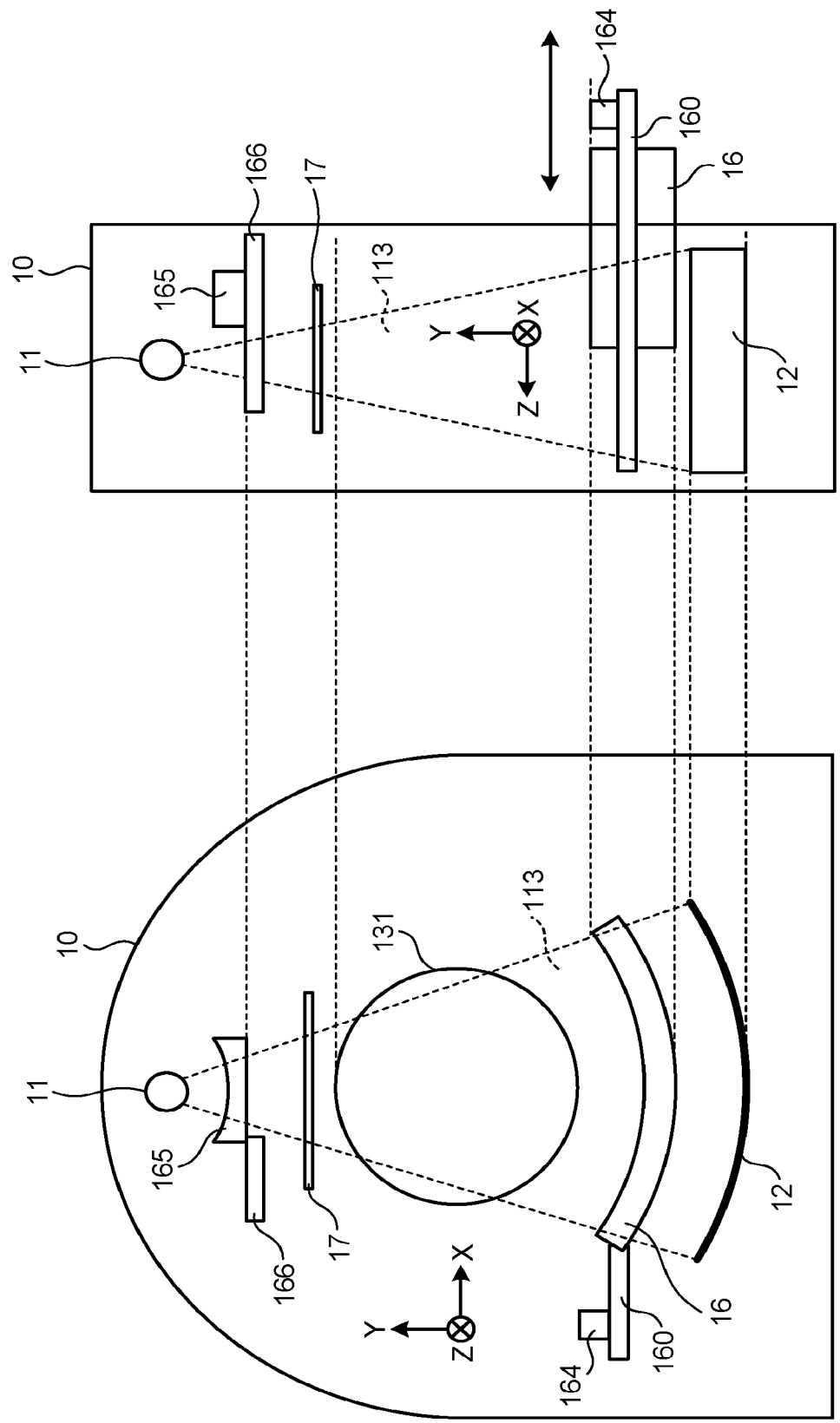
FIG. 18 is a diagram according to a modification example of the embodiment illustrating an example of a positional relationship among a supporting frame, a filter unit, and a wedge.

FIG. 18 is a diagram illustrating an example of a positional relationship among the supporting frame 160, the filter unit 16, and the wedge 165. The arrow in FIG. 18 indicates moving directions of the wedge 165 and the filter unit 16 at the time of moving into the X-ray radiation range 113 and retreating from the X-ray radiation range 113. As illustrated in FIG. 18, in a position lower than the couchtop 33, the supporting frame 160 is configured to support the filter unit 16 so as to be insertable into the X-ray radiation range 113. At the end of the energy calibrating process or in response to an instruction to start a scan on the patient P, the filter unit 16 is housed on the outside of the X-ray radiation range 113 by the supporting frame 160, while the wedge 165 is moved by a wedge supporting frame 166 into the X-ray radiation range 113. Further, in response to an instruction that the energy calibrating process be executed, the filter unit 16 is inserted in the X-ray radiation range 113, while the wedge 165 is moved by the wedge supporting frame 166 to the outside of the X-ray radiation range 113. Because the operation procedure and advantageous effects of the energy calibrating process according to the present modification example are the same as those of the embodiment, the explanations thereof will be omitted.

An Application Example

In the present application example, the X-ray imaging apparatus is realized as an X-ray diagnosis apparatus capable of generating an X-ray image such as a fluoroscopic image. The X-ray diagnosis apparatus according to the present application example is configured to perform a phase contrast imaging process, for example. Because the operation procedure and advantageous effects of the energy calibrating process according to the present application example are the same as those of the embodiment, the explanations thereof will be omitted.

The X-ray CT apparatuses 1 is available in various types such as a rotate/rotate type (a third generation CT) in which the X-ray tube 11 and the photon counting X-ray detector 12 integrally rotate around the patient P and a stationary/rotate type (a fourth generation CT) in which a large number of X-ray detecting elements in a ring-shaped array are fixed, while only the X-ray tube 11 rotates around the patient P. Any type is applicable to the present embodiments.

In addition, it is possible to realize the functions of the present embodiments by installing programs to execute the processes in a computer such as a workstation and loading the installed programs into a memory. In this situation, the programs capable of causing the computer to implement the method may be distributed as being stored in a storage medium such as a magnetic disk (a hard disk, etc.), an optical disk (e.g., a Compact Disk Read-Only Memory [CD-ROM] or a DVD), or a semiconductor memory.

When a technical concept of the present embodiments is realized as a monochromatic X-ray generating method, the monochromatic X-ray generating method includes: causing X-rays to become incident to the first filter 161 configured to shape a spectrum of the X-rays; causing X-rays related to the spectrum resulting from the shaping by the first filter 161 to become incident to the second filter 162 arranged on the X-ray exit side of the first filter 161; and causing the second filter 162 to generate monochromatic X-rays by using the X-rays related to the spectrum resulting from the shaping by the first filter 161. Because the operation procedure and advantageous effects of the monochromatic X-ray generating method are the same as those of the embodiment, the explanations thereof will be omitted. It is possible to utilize the monochromatic X-ray generating method in an energy calibrating process performed by a photon counting X-ray imaging apparatus.

According to at least one aspect of the embodiments described above, it is possible to efficiently and conveniently generate the X-rays that are nearly monochrome.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray imaging apparatus comprising:
    an X-ray tube configured to generate X-rays;
    a photon counting X-ray detector configured to count photons contained in the X-rays; and
    a filter unit provided between the X-ray tube and the photon counting X-ray detector, wherein
    the filter unit includes:
        a first filter configured to shape a spectrum of the X-rays; and
        a second filter configured to generate X-ray fluorescence on a basis of X-rays related to a spectrum resulting from the shaping by the first filter.

2. The X-ray imaging apparatus according to claim 1, further comprising: processing circuitry configured to calibrate outputs of a plurality of detecting elements included in the photon counting X-ray detector, on a basis of the X-ray fluorescence.

3. The X-ray imaging apparatus according to claim 1, wherein, with respect to the spectrum of the X-rays radiated from the X-ray tube, the first filter passes such X-rays that are in an energy region higher than energy of the X-ray fluorescence.

4. The X-ray imaging apparatus according to claim 1, wherein the first filter includes a plurality of types of metal.

5. The X-ray imaging apparatus according to claim 4, wherein the first filter includes one or both of aluminum and copper.

6. The X-ray imaging apparatus according to claim 1, wherein the second filter includes heavy metal.

7. The X-ray imaging apparatus according to claim 6, wherein the second filter includes one selected from a group consisting of molybdenum, tin, tungsten, and lead.

8. The X-ray imaging apparatus according to claim 1, wherein the filter unit is arranged between a couchtop and the X-ray tube, the couchtop being arranged between the X-ray tube and the photon counting X-ray detector.

9. The X-ray imaging apparatus according to claim 1, wherein the filter unit is arranged between a couchtop and the photon counting X-ray detector, the couchtop being arranged between the X-ray tube and the photon counting X-ray detector.

10. The X-ray imaging apparatus according to claim 8, further comprising:
    a supporting frame configured to support the filter unit so as to be insertable in a radiation range of the X-rays generated by the X-ray tube; and
    processing circuitry configured to control moving of a wedge filter to an outside of the radiation range and moving of the filter unit into the radiation range.

11. A monochromatic X-ray generating method comprising:
    causing X-rays to become incident to a first filter configured to shape a spectrum of the X-rays;
    causing X-rays related to a spectrum resulting from the shaping by the first filter to become incident to a second filter arranged on an X-ray exit side of the first filter; and
    causing a second filter to generate monochromatic X-rays by using the X-rays related to the spectrum resulting from the shaping by the first filter.

* * * * *